US012635869B2

(12) United States Patent
Awadu

(10) Patent No.: US 12,635,869 B2
(45) Date of Patent: May 26, 2026

(54) SAFE AND SECURE METHOD FOR INSERTING DEVICES INTO HOLLOW ORGANS AND BODY CAVITIES

(71) Applicant: Satoshi Awadu, Nagasaki (JP)

(72) Inventor: Satoshi Awadu, Nagasaki (JP)

( * ) Notice: Subject to any disclaimer, the term of this patent is extended or adjusted under 35 U.S.C. 154(b) by 190 days.

(21) Appl. No.: 18/740,994

(22) Filed: Jun. 12, 2024

(65) Prior Publication Data

US 2024/0341583 A1     Oct. 17, 2024

Related U.S. Application Data

(63) Continuation-in-part of application No. 16/998,392, filed on Aug. 20, 2020, now Pat. No. 12,048,425.

(51) Int. Cl.
| | |
|---|---|
| *A61B 1/247* | (2006.01) |
| *A61B 1/233* | (2006.01) |
| *A61B 1/273* | (2006.01) |
| *A61B 17/00* | (2006.01) |
| *A61M 16/04* | (2006.01) |

(52) U.S. Cl.
CPC ............... *A61B 1/247* (2013.01); *A61B 1/233* (2013.01); *A61B 1/2736* (2013.01); *A61B 17/00234* (2013.01); *A61M 16/049* (2014.02); *A61B 2017/00296* (2013.01); *A61B 2017/00353* (2013.01); *A61B 2017/00818* (2013.01)

(58) Field of Classification Search
None
See application file for complete search history.

(56) References Cited

U.S. PATENT DOCUMENTS

| | | | |
|---|---|---|---|
| 4,577,621 | A | 3/1986 | Patel |
| 5,078,743 | A | 1/1992 | Mikalov et al. |
| 5,599,304 | A | 2/1997 | Shaari |
| 5,624,439 | A | 4/1997 | Edwards et al. |
| 5,816,257 | A | 10/1998 | Chin |
| 5,842,973 | A | 12/1998 | Bullard |
| 5,855,207 | A | 1/1999 | Moenning et al. |
| 6,053,172 | A | 4/2000 | Hovda et al. |
| 9,561,055 | B1 | 2/2017 | Karim |
| 2003/0040681 | A1 | 2/2003 | Ng et al. |
| 2003/0220551 | A1 | 11/2003 | Kimball et al. |
| 2004/0035429 | A1 | 2/2004 | Wakabayashi |

(Continued)

OTHER PUBLICATIONS

Safiruddin-Koutsourelakis-Vries <Upper airway collapse during drug induced sleep endoscopy> 2014.

(Continued)

*Primary Examiner* — John P Leubecker
(74) *Attorney, Agent, or Firm* — Renner, Otto, Boisselle & Sklar, LLP

(57)     ABSTRACT

A device insertion method for observing the lateral wall of the lumen includes: rotating a hollow organ by changing a body position; turning the tip of the device to the lateral wall of the lumen by rotating the device; and retracting the organ with the device itself by rotating the device, In other embodiments, an endoscope insertion method for observing the lateral side of the organ includes: rotating a body cavity by changing a body position; turning the tip of the flexible endoscope to the lateral side of the organ by rotating the flexible endoscope; and retracting the organ with the flexible endoscope itself by rotating the flexible endoscope.

14 Claims, 13 Drawing Sheets

(56) References Cited

U.S. PATENT DOCUMENTS

| | | |
|---|---|---|
| 2004/0127800 A1 | 7/2004 | Kimball et al. |
| 2006/0063973 A1 | 3/2006 | Makower et al. |
| 2006/0235352 A1 | 10/2006 | Dziewas et al. |
| 2007/0083225 A1 | 4/2007 | Kiser et al. |
| 2007/0137654 A1 | 6/2007 | Paraschac et al. |
| 2007/0137655 A1 | 6/2007 | Paraschac et al. |
| 2007/0250105 A1 | 10/2007 | Ressemann et al. |
| 2008/0249359 A1 | 10/2008 | Abraham-Fuchs et al. |
| 2009/0227864 A1 | 9/2009 | Sato et al. |
| 2010/0174366 A1 | 7/2010 | Avior |
| 2010/0331619 A1 | 12/2010 | Miyoshi et al. |
| 2013/0027531 A1 | 1/2013 | Miyoshi et al. |
| 2014/0039259 A1 | 2/2014 | Okaniwa |
| 2014/0249464 A1 | 9/2014 | Godin |
| 2015/0342445 A1 | 12/2015 | Jones et al. |
| 2017/0119582 A1 | 5/2017 | Chan et al. |
| 2018/0125560 A1 | 5/2018 | Saadat et al. |
| 2018/0338806 A1 | 11/2018 | Grubbs |
| 2019/0254563 A1 | 8/2019 | Nakamitsu et al. |
| 2020/0000316 A1 | 1/2020 | Ikeda et al. |
| 2020/0093353 A1 | 3/2020 | Tezuka et al. |
| 2020/0129046 A1 | 4/2020 | Sinay et al. |
| 2020/0138269 A1 | 5/2020 | Nishimura |
| 2022/0400931 A1* | 12/2022 | Hane .................. A61B 1/0016 |

OTHER PUBLICATIONS

Awazu et al., "A linear sigmoid colon passage method by left twisting", Awazu Hospital, Nagasaki, Japan, PeerJ PrePrints, Nov. 12, 2013.

Awazu et al., "A linear sigmoid colon passage method in colonoscopy", Awazu Hospital, Nagasaki, Japan, PeerJ PrePrints, Oct. 13, 2014.

Awazu et al., "A method of linear passage through the sigmoid colon in colonoscopy", Gastrointestinal Endoscopy, pp. 702-704, vol. 75, No. 3, 2012.

Allowed Claims of parent U.S. Appl. No. 16/998,392, filed Aug. 20, 2020.

U.S. Appl. No. 16/998,392, filed Aug. 20, 2020.

* cited by examiner

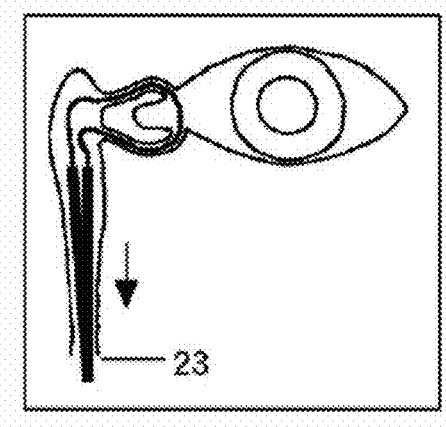
Fig. 6A
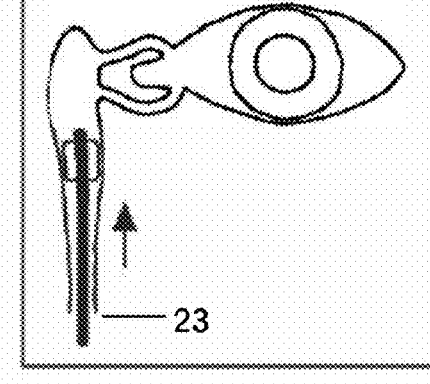
Fig. 6B
Fig. 7
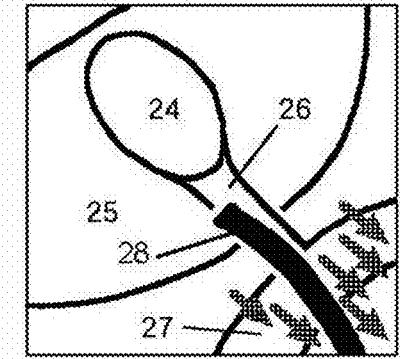

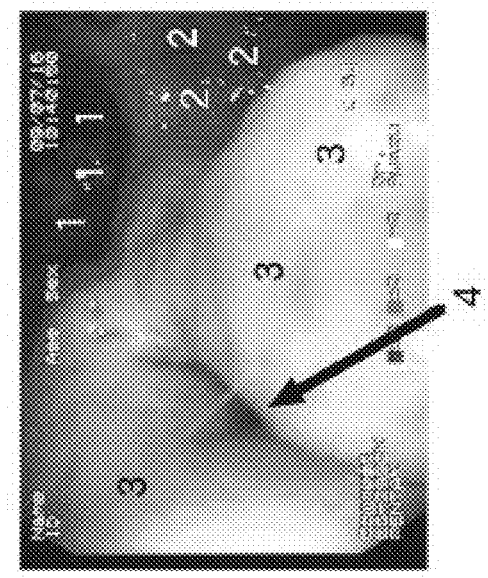
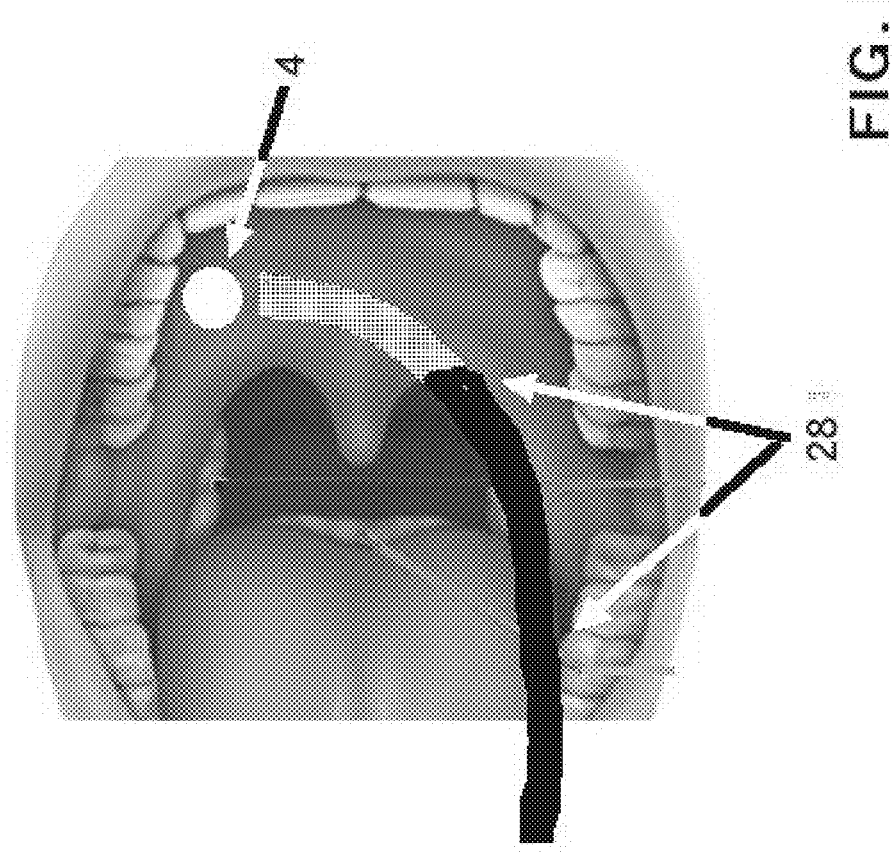
FIG. 8

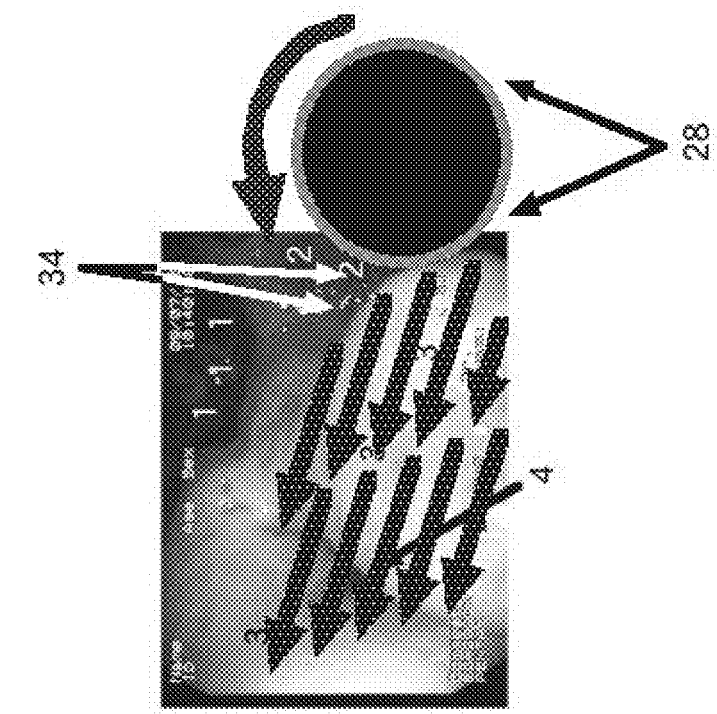
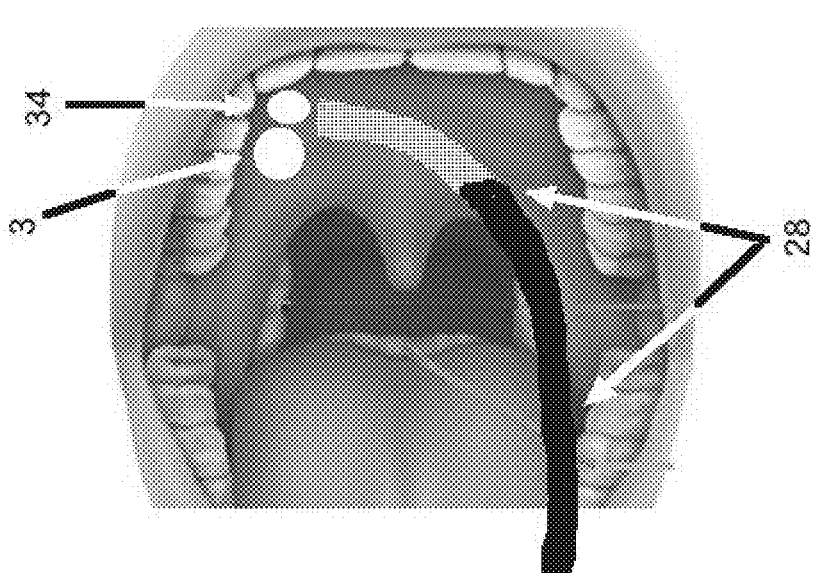
FIG. 11

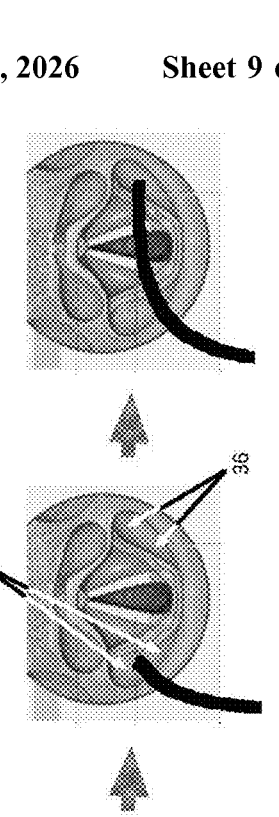
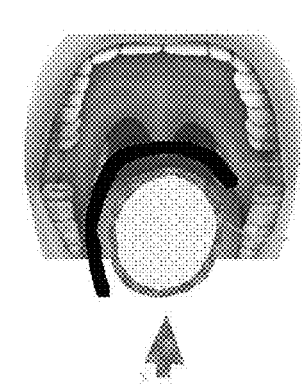
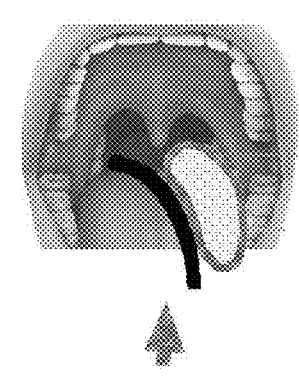
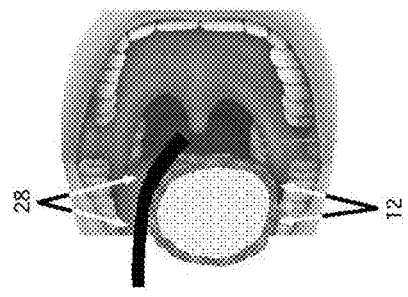
FIG. 12

SAFE AND SECURE METHOD FOR INSERTING DEVICES INTO HOLLOW ORGANS AND BODY CAVITIES

CROSS REFERENCE TO RELATED APPLICATIONS

This application is a Continuation-In-Part of U.S. Pat. No. 12,048,425, the disclosure of which is hereby incorporated herein by reference in its entirety.

TECHNICAL FIELD

The present invention relates to the flexible endoscopic diagnosis and treatment.

BACKGROUND OF THE INVENTION

Malignant tumors of the Eustachian tube, tympanic cavity, mastoid antrum, maxillary sinus, frontal sinus, sphenoidal sinus, ethmoidal sinus, nasolacrimal duct, or lachrymal sac have not been diagnosed systematically, and their prognosis has been poor. Therefore, the establishment of a system for their diagnosis and treatment has been needed.

First, in the patient with carcinogenic risk due to chronic inflammatory disease of the Eustachian tube, tympanic cavity, mastoid antrum, maxillary sinus, frontal sinus, sphenoidal sinus, ethmoidal sinus, nasolacrimal duct, or lachrymal sac, the endoscopic diagnosis has been needed before the stage in which they become detectable by PET-CT or PET-MRI, for example, 5 mm in diameter. Also, tumors of the Eustachian tube, tympanic cavity, mastoid antrum, maxillary sinus, frontal sinus, sphenoidal sinus, ethmoidal sinus, nasolacrimal duct, or lachrymal sac 10 mm in diameter can be detected by using PET-CT or PET-MRI and can be treated by using proton therapy or carbon ion radiotherapy. Therefore, the endoscopic diagnosis of these tumors has been needed.

Transnasal flexible endoscopic observation of the pharyngeal orifice of the Eustachian tube, the Rosenmüller's fossa, or the roof of the nasal cavity, and transoral flexible endoscopic observation of the tonsillar fossa or the oral cavity may be occasionally difficult due to the presence of blind areas. Therefore, the new insertion method has been needed.

Tumorectomy for the pathological diagnosis in the Eustachian tube, tympanic cavity, mastoid antrum, maxillary sinus, frontal sinus, sphenoidal sinus, ethmoidal sinus, nasolacrimal duct, or lachrymal sac, branchial fistulectomy for the treatment of second branchial cleft fistula, transpalatal repair of basal skull base herniation for the treatment of persistent craniopharyngeal canal, transcatheter arterial embolization for the treatment of posterior epistaxis, the surgical treatment of skull base cerebrospinal fluid leak, palatal obturator insertion for the treatment of oronasal fistula, mastoidectomy for the treatment of mastoiditis, transcanalicular balloon catheter dilation of the nasolacrimal duct for the treatment of nasolacrimal duct obstruction, transcanalicular nasolacrimal duct recanalization for the treatment of nasolacrimal duct obstruction, transcanalicular nasolacrimal silicone stent intubation for the treatment of nasolacrimal duct obstruction have been invasive. Therefore, the new flexible endoscopic procedure has been needed.

Transnasal balloon catheter insertion into the Eustachian tube for the treatment of Eustachian tube dysfunction, transnasal laser catheter insertion into the Eustachian tube for the treatment of Eustachian tube dysfunction, transnasal endoscopic injection into the torus tubarius for the treatment of patulous Eustachian tube, surgical transtympanic catheter insertion into the Eustachian tube for the treatment of patulous Eustachian tube have occasionally been difficult. Therefore, the new flexible endoscopic procedure has been needed.

The nasopharynx or nasal cavity have not been examined in transoral flexible gastroscopy, and when a transnasal flexible endoscope cannot be inserted due to the obstruction and said flexible endoscope is transorally inserted, the obstructive disorder has not been diagnosed. Therefore, the new insertion method has been needed.

Flexible endoscopic diagnosis and treatment of the lateral wall of the hypopharynx, larynx, trachea, bronchus, bile duct, pancreatic duct, duodenum, stomach, esophagus, urethra, bladder, ureter, renal pelvis, vagina, and uterus has been difficult. Therefore, the new insertion method has been needed.

Flexible endoscopic retraction method for securing the broader operative field has been needed in natural orifice transluminal endoscopic surgery or single-incision flexible endoscopic surgery.

Flexible endoscopic diagnosis and treatment of the pyriform sinus has been difficult. Therefore, the new endoscope insertion method has been needed.

Flexible endoscopic diagnosis and treatment of the post-cricoid region and the posterior wall of the hypopharynx has been difficult. Therefore, the new endoscope insertion method has been needed.

Tracheal intubation has been difficult when the laryngoscope blade cannot be inserted due to trismus, micrognathia, oral tumor, tongue tumor, tonsil enlargement, oropharyngeal tumor, hypopharyngeal tumor, or thyroid tumor. Therefore, the new tracheal tube insertion method has been needed.

Hypertension, tachycardia, or vagal reflex due to laryngeal expansion has been invasive. Therefore, the new tracheal tube insertion method has been needed.

Hypoxemia due to esophageal intubation has been fatal. Therefore, the new tracheal tube insertion method has been needed.

When a patient with a full stomach vomited during tracheal intubation, there has been a risk of aspiration. Therefore, the new tracheal tube insertion method has been needed.

When performing general anesthesia, there has been a risk of hypoxemia due to mask ventilation failure after administration of muscle relaxants. Therefore, the new tracheal tube insertion method has been needed.

In transoral gastroscopy, pain, hypertension, or tachycardia due to gag reflex, respiratory depression, hypotension, or bradycardia due to sedatives have been invasive. Therefore, the new gastroscope insertion method has been needed.

When the transnasal gastroscope cannot be inserted, the transoral gastroscope must be inserted, which meant a double hassle. Therefore, the new gastroscope insertion method has been needed.

BRIEF SUMMARY OF THE INVENTION

In the present invention, the diagnosis and treatment of the lateral wall of the lumen can be performed by changing the body position, rotating the flexible endoscope in the counter direction of the lumen, and retracting the organ with the flexible endoscope itself. Also, the diagnosis and treatment of the lateral side of the organ can be performed by changing the body position, rotating the flexible endoscope in the direction of the lateral side of the organ, and retracting the organ with the flexible endoscope itself.

Problems to be Resolved by the Invention

To provide novel methods for the diagnosis and treatment by using the endoscope.

MEANS OF SOLVING THE PROBLEMS

In accordance with an aspect of the present disclosure, a flexible endoscope insertion method comprises: (a) rotating a hollow organ by 45 to 90 degrees by changing the body position to the semilateral position or the lateral position for observing the lateral wall of the lumen, wherein the previous body position was the supine, semi-recumbent, sitting, litho-tripsy, or prone position; (b) turning the tip of the flexible endoscope to the lateral wall of the lumen by rotating the hand-held or holding portion of the flexible endoscope in the counter direction of the lumen; and (c) retracting the organ with the flexible endoscope itself by rotating the flexible endoscope in the counter direction of the lumen for securing the visual field.

Right or left turns of the endoscope are accomplished by twisting the body (i.e. the hand-held or holding portion) of the endoscope to the right (clockwise, from the perspective of the person holding the endoscope) or left (counter-clockwise) direction using the right hand. The body of the endoscope is grasped in the right hand, angling the tip using the inner control knob using the left hand. Similarly, apply-ing a twisting (right or left) motion when the tip is deflected upward has the effect of turning the endoscope to the right or left without using the left/right control knob. Alterna-tively, the outer control knob (left/right) can be used. In other words, if the tip is to be turned to the right, the holding portion of the flexible endoscope is rotated clockwise.

In some embodiments, (b) comprises: inserting the flex-ible endoscope into a next lumen while rotating the flexible endoscope in the direction of the lumen; turning the tip of the flexible endoscope to the lateral wall of the next lumen by rotating the flexible endoscope in the counter direction of the lumen; and examining the lateral wall of the next lumen. In some embodiments, the flexible endoscope insertion method comprises the steps of: placing the patient in the left lateral position; inserting the flexible endoscope into the nasopharynx while rotating the flexible endoscope to the right; turning the tip of the flexible endoscope to the right lateral wall of the nasopharynx by rotating the flexible endoscope to the left; and examining the pharyngeal orifice of the right Eustachian tube.

In some embodiments, (b) comprises turning the tip of the flexible endoscope by rotating the flexible endoscope by 360 degrees in the counter direction of the lumen, wherein more larger looping of the flexible endoscope is made in the lumen. In some embodiments, the pharyngeal orifice of the Eustachian tube can be observed from a front by rotating the flexible endoscope by 360 degrees in the counter direction of the lumen in the oropharymgeo-nasopharyngeal cavity, and wherein more larger looping of the flexible endoscope is made in the oropharymgeo-nasopharyngeal cavity; In some embodiments, the flexible endoscope insertion method com-prises the steps of: placing the patient in the left lateral position; inserting the flexible endoscope into the orophar-ynx; turning the tip of the flexible endoscope to the left by rotating or twisting the flexible endoscope to the left (coun-terclockwise) by 90 degrees; further more turning the tip of the flexible endoscope to the left by rotating the flexible endoscope to the left (counterclockwise) by 180 degrees; inserting the flexible endoscope into the nasopharynx while rotating the flexible endoscope to the left by 90 degrees; and directing the tip of the flexible endoscope to the right lateral wall of the nasopharynx; examining the pharyngeal orifice of the right Eustachian tube.

In some embodiments, the flexible endoscope is tran-sorally inserted into the nasopharnx, the Rosenmüller's fossa, the persistent craniopharyngeal canal, the Eustachian tube, the tympanic cavity, the mastoid antrum, the nasal cavity; the maxillary sinus, the frontal sinus, the sphenoidal sinus, the ethmoidal sinus, the nasolacrimal duct, or the lachrymal sac. In some embodiments, the flexible endoscope insertion method comprises the steps of: placing the patient in the left lateral position; inserting the flexible endoscope into the nasopharynx while rotating or twisting the flexible endoscope to the right (clockwise); and inserting the flexible endoscope into the nasal cavity. In some embodiments, the flexible endoscope insertion method comprises the steps of: placing the patient in the right lateral position; inserting the flexible endoscope into the nasopharynx while rotating the flexible endoscope to the left (counterclockwise); and insert-ing the flexible endoscope into the nasal cavity.

In some embodiments, the tonsillar fossa can be observed from a front by medially retracting the tongue with the flexible endoscope itself. In some embodiments, the flexible endoscope insertion method comprises the steps of: placing the patient in the left lateral position; inserting the flexible endoscope through the mouth into the oropharynx; rotating the flexible endoscope to the right so as to be observed the palatine uvula in the direction of 12 o'clock for positioning the flexible endoscope on the lateral side of the tongue; gradually rotating the flexible endoscope to the left while maintaining a slight distance between the flexible endoscope and the right posterior palatine arch for medially retracting the tongue with the flexible endoscope itself; inserting the flexible endoscope into the right tonsillar fossa by slightly pushing the flexible endoscope; and examining the right tonsillar fossa.

In some embodiments, the lateral palatine region, the maxillary linguogingival region and the incisive papilla region can be observed from a front by rotating the flexible endoscope in the counter direction of the lumen in the oral cavity, wherein the flexible endoscope looping is made in the oral cavity.

In some embodiments, the flexible endoscope is inserted into the hypopharynx, larynx, trachea, bronchus, bile duct, pancreatic duct, duodenum, stomach, esophagus, urethra, bladder, ureter, renal pelvis, vagina, uterus, or fallopian tube.

In some embodiments, a device used in the method comprises: a tube with a nozzle that can spray over an area of 15-25 mm in diameter from a distance of 15-20 mm, an endoscope with a nozzle that can spray over an area of 15-25 mm in diameter from a distance of 15-20 mm, a nasal plug 7-12 mm in diameter, a flexible endoscope, biopsy forceps, a high-frequency electric knife, a laser catheter, a balloon catheter, a drill, a high speed drill, an endoscopic clip, a tube for the treatment of second branchial cleft fistula, wherein the drug is infused through the internal opening of the second branchial cleft fistula that opens in the tonsillar region, a plug for closing persistent craniopharyngeal canal, a plug for closing cerebrospinal fluid fistula in the treatment of skull base cerebrospinal fluid leak, a plug for closing oronasal fistula, an indwelling drainage catheter for the treatment of mastoiditis, an indwelling drainage catheter for the treatment of sinusitis, a balloon catheter which is inserted through the nasolacrimal duct ostium for the treatment of nasolacrimal duct obstruction, a probe which is inserted through the nasolacrimal duct ostium for the treatment of nasolacrimal duct obstruction, a silicone stent or metallic stent which is inserted through the nasolacrimal duct ostium for the a treatment of nasolacrimal duct obstruction, a balloon catheter and laser catheter for the treatment of Eustachian tube dysfunction, an indwelling catheter for the treatment of Eustachian tube dysfunction, an injection needle for injecting into the torus tubarius in the treatment of patulous Eustachian tube, a catheter for the treatment of patulous Eustachian tube, and a flexible endoscope made of an anti-slip material for retracting the organ.

In accordance with another aspect of the present disclosure, a flexible endoscope insertion method, comprises: (a) rotating a body cavity by 0 to 90 degrees by changing the body position to the appropriate position for observing the lateral side of the organ, wherein the previous body position was the arbitrary body position; (b) turning the tip of the flexible endoscope to the lateral side of the organ by rotating the flexible endoscope in the direction of the lateral side of the organ; and (c) retracting the organ with the flexible endoscope itself by rotating the flexible endoscope in the direction of the lateral side of the organ for securing the visual field.

In some embodiments, (b) and (c) comprise: turning the tip of the flexible endoscope to the lateral side of the organ by rotating the flexible endoscope in the direction of the lateral side of the organ while retracting the organ with the flexible endoscope itself by rotating the flexible endoscope in the direction of the lateral side of the organ for securing the visual field. In some embodiments, the lateral side of the organ can be observed from a front by retracting the organ with the flexible endoscope itself in natural orifice transluminal endoscopic surgery or single-incision flexible endoscopic surgery.

In some embodiments, a device used in the method comprises: a flexible endoscope, biopsy forceps, a high-frequency electric knife, a high-frequency electric hook, a retractor, a grasping forceps, a dissecting forceps, an ultrasonic dissector, a water jet dissector, a bulldog clamp forceps, an endoscopic clip, a scissor, a suture forceps, a laser catheter, a balloon catheter, a drill, a high speed drill, a flexible endoscope made of an anti-slip material for retracting the organ, a port wherein the sliding tube for colonoscopy is shortened to about a few centimeters and the port is placed in the body wall and the flexible endoscope is inserted through the port into the body cavity, a cryoprobe, and a radiofrequency probe.

Effects of the Invention

According to the present invention, the advanced flexible endoscopic diagnosis and treatment can be performed.

BRIEF DESCRIPTION OF THE DRAWINGS

FIGS. 4A, 4B, and 4C are systematic diagrams showing insertion routes of the flexible endoscope.

FIG. 5A is an image showing transtympanic catheter insertion into the Eustachian tube.

FIG. 5B is an image showing endoscopic transoral transpharyngeal catheter insertion into the Eustachian tube.

FIG. 6A is an image showing the silicone stent intubation through the lachrymal punctum.

FIG. 6B is an image showing the silicone stent intubation through the nasolacrimal duct ostium.

FIG. 7 is an image showing the state of retracting the duodenum, transverse colon, and greater omentum and stretching the right lateral side of the common bile duct.

FIG. 8 is an image showing turning the tip of the flexible endoscope to the pharyngeal orifice of the right Eustachian tube.

Figure 9:
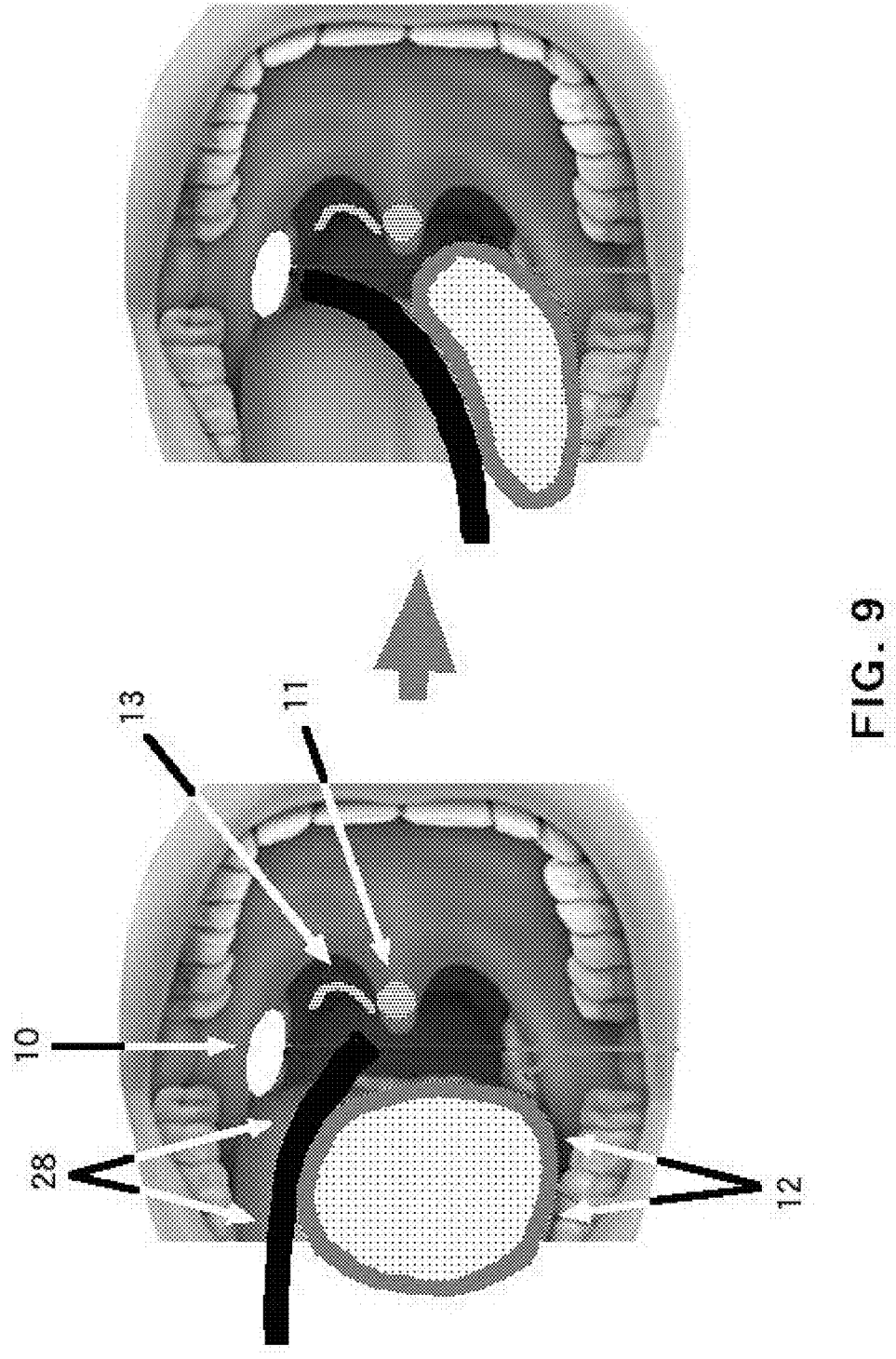

FIG. 9 is an image showing retracting the tongue and turning the tip of the flexible endoscope to the right tonsillar fossa.

Figure 10:
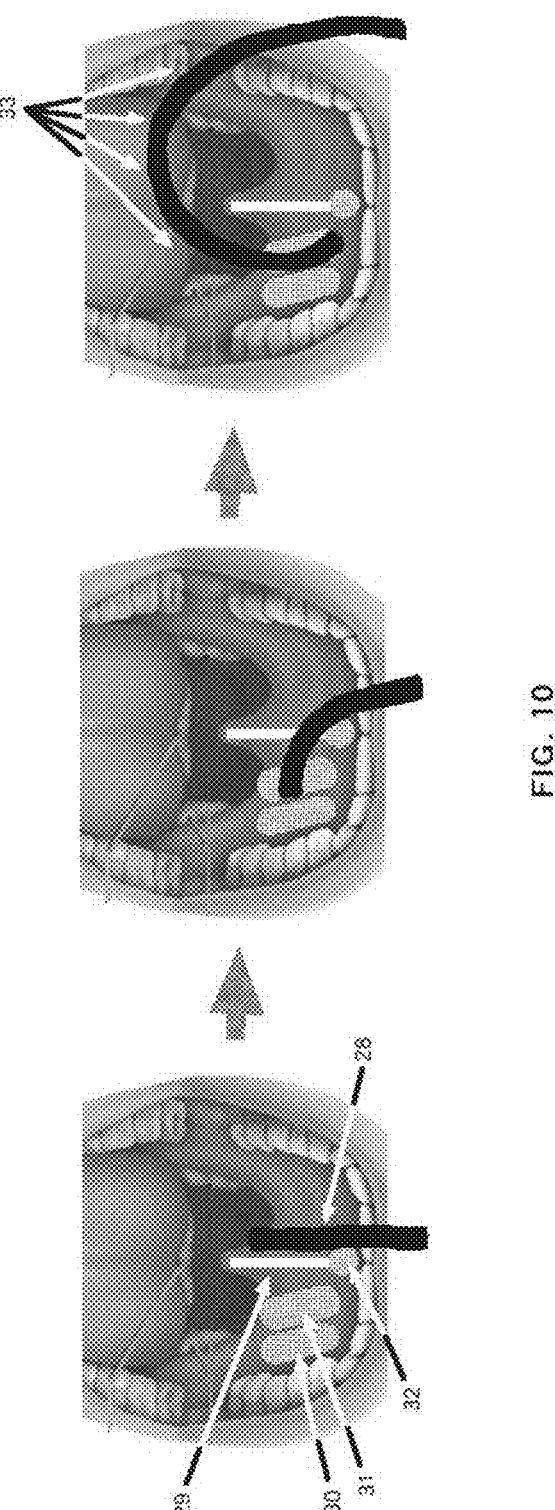

FIG. 10 is an image showing observing a lateral palatine region, a maxillary linguogingival region and a incisive papilla region by rotating the flexible endoscope by 360 degrees.

FIG. 11 is an image showing the state of retracting the right torus tubarius and inserting the flexible endoscope into the right Rosenmüller's fossa.

FIG. 12 is an image showing the state of retracting the tongue and inserting the flexible endoscope into the right pyriform sinus.

Figure 13A:
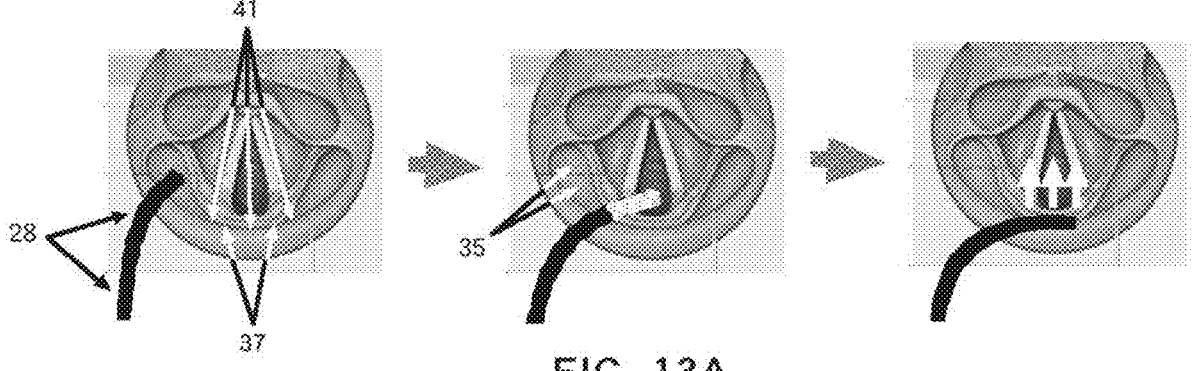

FIG. 13A is an image showing the state of inserting the flexible endoscope into the esophagus, retracting the cricoid cartilage by pulling the flexible endoscope while applying an upward angle and inserting the flexible endoscope between the cricoid cartilage and the posterior wall of the hypopharynx.

Figure 13B:
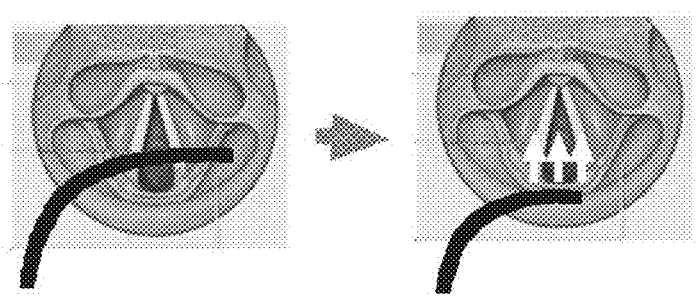

FIG. 13B is an image showing the state of retracting the cricoid cartilage by pushing the flexible endoscope while applying a downward angle and inserting the flexible endoscope between the cricoid cartilage and the posterior wall of the hypopharynx.

Figure 13C:
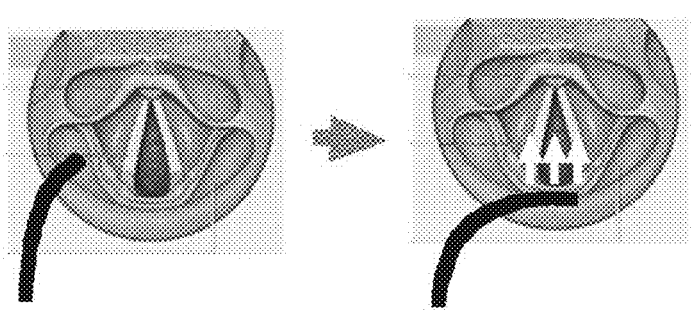

FIG. 13C is an image showing the state of retracting the cricoid cartilage by pushing the flexible endoscope while applying an upward angle and inserting the flexible endoscope between the cricoid cartilage and the posterior wall of the hypopharynx.

Figures 14A, 14B:

FIG. 14A is an image showing the state of retracting the tongue and inserting the tracheal tube into the trachea FIG. 14B is an image showing the state of inserting the tracheal tube into the trachea in conventional insertion method.

Figures 15A, 15B:
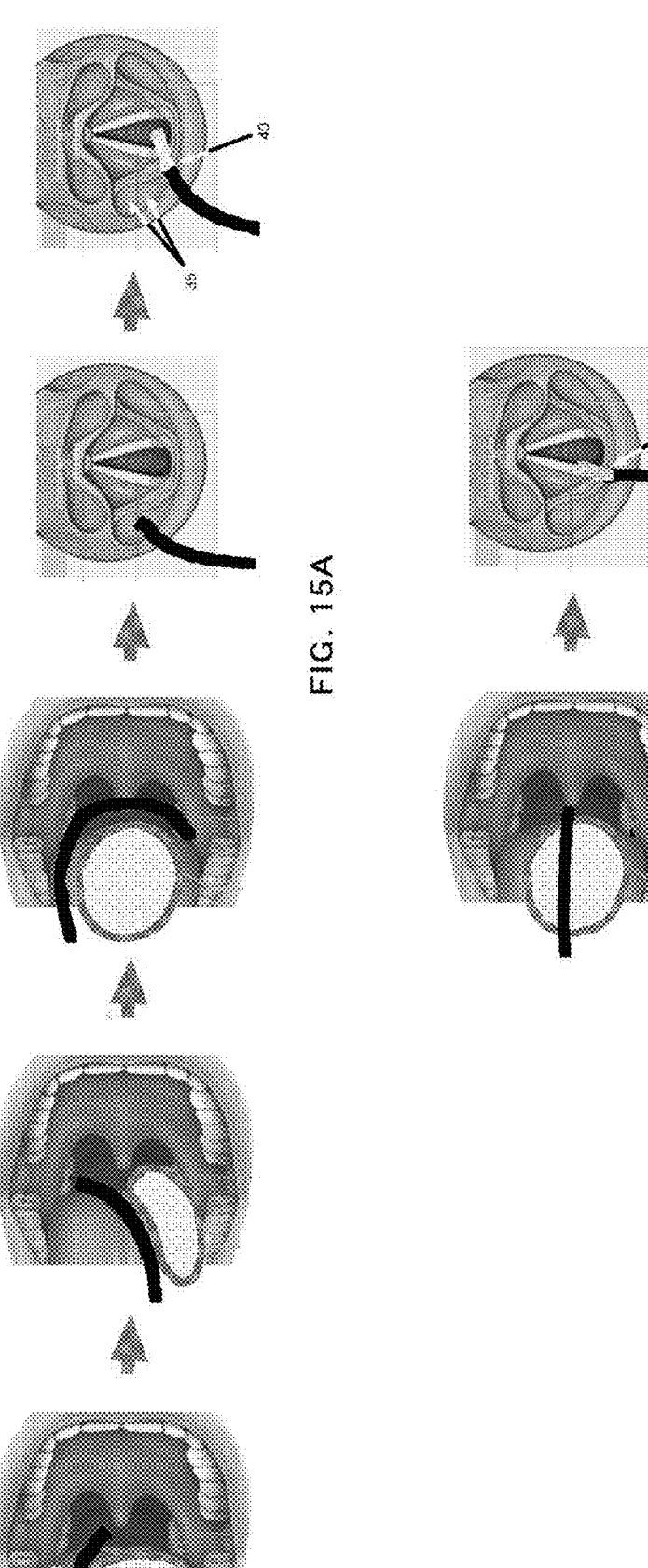

FIG. 15A is an image showing the state of retracting the tongue and inserting the gastroscope through the left pyriform sinus into the esophagus.

FIG. 15B is an image showing the state of inserting the gastroscope into the esophagus in conventional insertion method.

Figure 16:
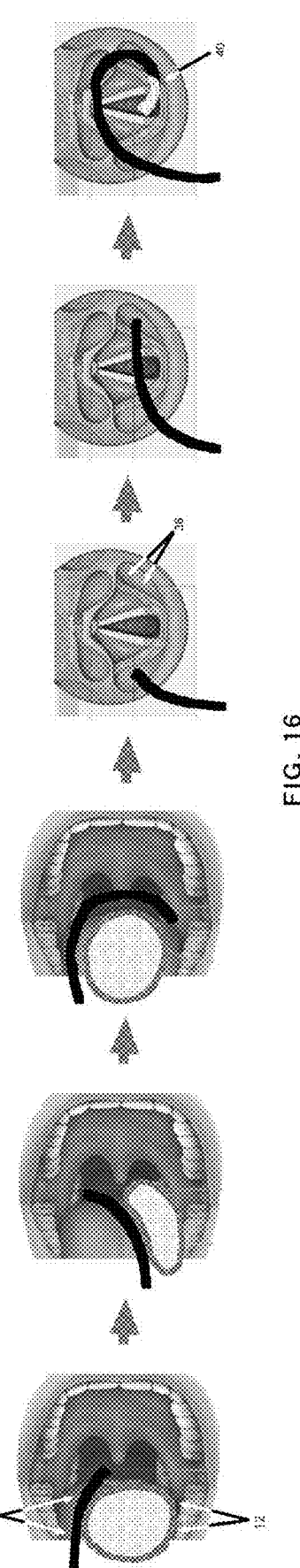

FIG. 16 is an image showing the state of retracting the tongue and inserting the gastroscope through the right pyriform sinus into the esophagus.

DETAILED DESCRIPTION OF THE INVENTION

In the present invention, flexible gastroscope, flexible bronchoscope, flexible laryngoscope, flexible nasopharyngoscope, flexible enteroscope, flexible cholangioscope, flexible pancreatoscope, flexible cystoscope, flexible ureteroscope, flexible hysteroscope, and flexible endoscope for natural orifice transluminal endoscopic surgery can be used, but are not restricted to them.

The present invention includes the operation of retracting organs that interrupt the visual field. Organs to be retracted include the tongue, soft palate, torus tubarius, esophagus, stomach, duodenum, small intestine, large intestine, liver, gallbladder, bile duct, pancreas, spleen, adrenal gland, kidney, renal pelvis, ureter, bladder, deferent duct, seminal vesicle, prostate, uterus, vagina, ovary, fallopian tube, lung, trachea, bronchus, thymus, atrium, ventricle, diaphragm, abdominal rectus muscle, abdominal external oblique muscle, abdominal internal oblique muscle, abdominal transverse muscle, greater omentum, mesenterium, artery, vein, nerve, lymph node, and fat but are not restricted to them.

In the present invention, the thickness of the flexible endoscope inserted into the oropharynx, nasopharynx, nasal cavity, Eustachian tube, tympanic cavity, mastoid antrum, maxillary sinus, frontal sinus, sphenoidal sinus, ethmoidal sinus, nasolacrimal duct, and lachrymal sac is preferably 0.5 mm or greater, and more preferably 2.5 mm or greater, and even more preferably 3 mm or greater in minimum diameter, and preferably 15 mm or less, and more preferably 10 mm or less, and even more preferably 6 mm or less in maximum diameter. And it is desirable to use an elastic flexible endoscope about 5 mm in diameter for retracting organs which is surrounded by the cartilage such as the Rosenmüller's fossa or nasal concha, and it is desirable to use a thin flexible endoscope about 3 mm in diameter for examining the narrow site which is surrounded by the bone or the ligament.

In the present invention, flexible endoscopes are preferably equipped with a nozzle for spraying the anesthetic. The minimum spraying distance is preferably 15 mm or more, more preferably 16 mm or more, and even more preferably 17 mm or more, and the maximum spraying distance is preferably 20 mm or less, more preferably 19 mm or less, and even more preferably 18 mm or less. The area sprayed with the anesthetic is preferably 15 mm or more, more preferably 17 mm or more, and even more preferably 19 mm or more in minimum diameter and preferably 25 mm or less, more preferably 23 mm or less, and even more preferably 21 mm or less in maximum diameter.

Spraying angle that can spray over an area of 15-25 mm in diameter from a distance of 15-20 mm is most preferably. To make this possible, the minimum spraying angle is preferably 40 degrees or more, more preferably 50 degrees or more, and even more preferably 55 degrees or more, the maximum spraying angle is preferably 75 degrees or less, more preferably 70 degrees or less, and even more preferably 65 degrees or less.

In the present invention, malignant tumors of the Eustachian tube, tympanic cavity, mastoid antrum, maxillary sinus, frontal sinus, sphenoidal sinus, ethmoidal sinus, nasolacrimal duct, or lachrymal sac can be systemically diagnosed and treated.

First, in the patient with carcinogenic risk due to chronic inflammatory disease of the Eustachian tube, tympanic cavity, mastoid antrum, maxillary sinus, frontal sinus, sphenoidal sinus, ethmoidal sinus, nasolacrimal duct, or lachrymal sac, early diagnosis of these tumors can be performed before the stage in which they become detectable by PET-CT or PET-MRI, for example, 5 mm in diameter.

Also, tumors of the Eustachian tube, tympanic cavity, mastoid antrum, maxillary sinus, frontal sinus, sphenoidal sinus, ethmoidal sinus, nasolacrimal duct, or lachrymal sac 10 mm in diameter, which is detected by using PET-CT or PET-MRI, can be diagnosed by using the transorally inserted flexible endoscope and can be treated by using proton therapy or carbon ion radiotherapy.

Figure 1:
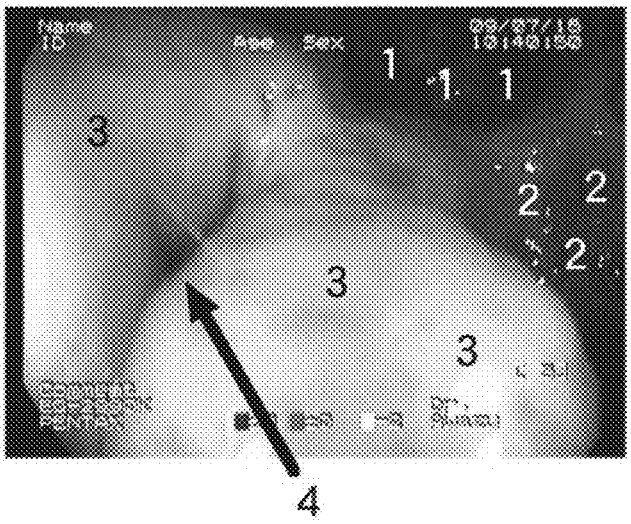
FIG. 1 is a frontal view of the pharyngeal orifice of the right Eustachian tube in the nasopharynx.
Figure 2:
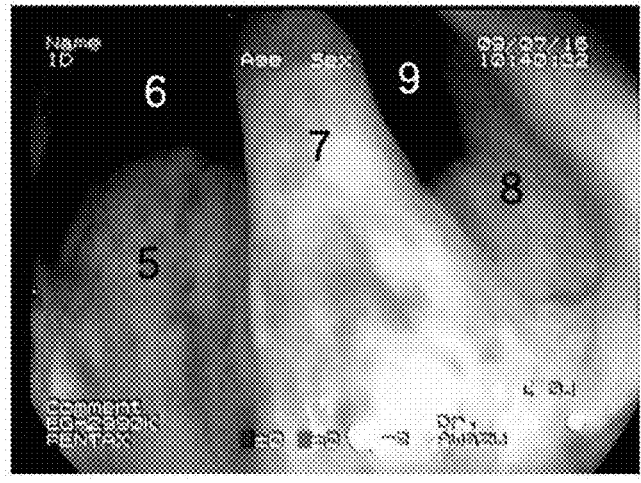
FIG. 2 is a frontal view of the roof of the nasal cavity.
Figure 3:
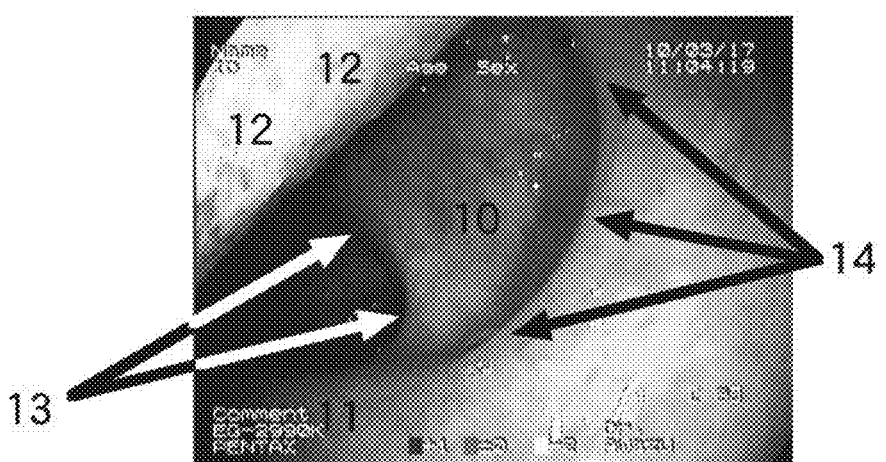
FIG. 3 is a frontal view of the right tonsillar fossa.

In the present invention, the endoscopic observation of the conventionally unexamined areas (such as the pharyngeal orifice of the Eustachian tube (FIG. 1), the Rosenmüller's fossa, the roof of the nasal cavity (FIG. 2), the tonsillar fossa (FIG. 3), or the oral cavity) can be performed by using the transorally inserted flexible endoscope. And images are vertically and horizontally reversed, for example, the right nasal cavity is observed in the left of the screen and the roof of the nasal cavity is observed from the front (FIG. 2), but this poses no problem.

Figure 4A:
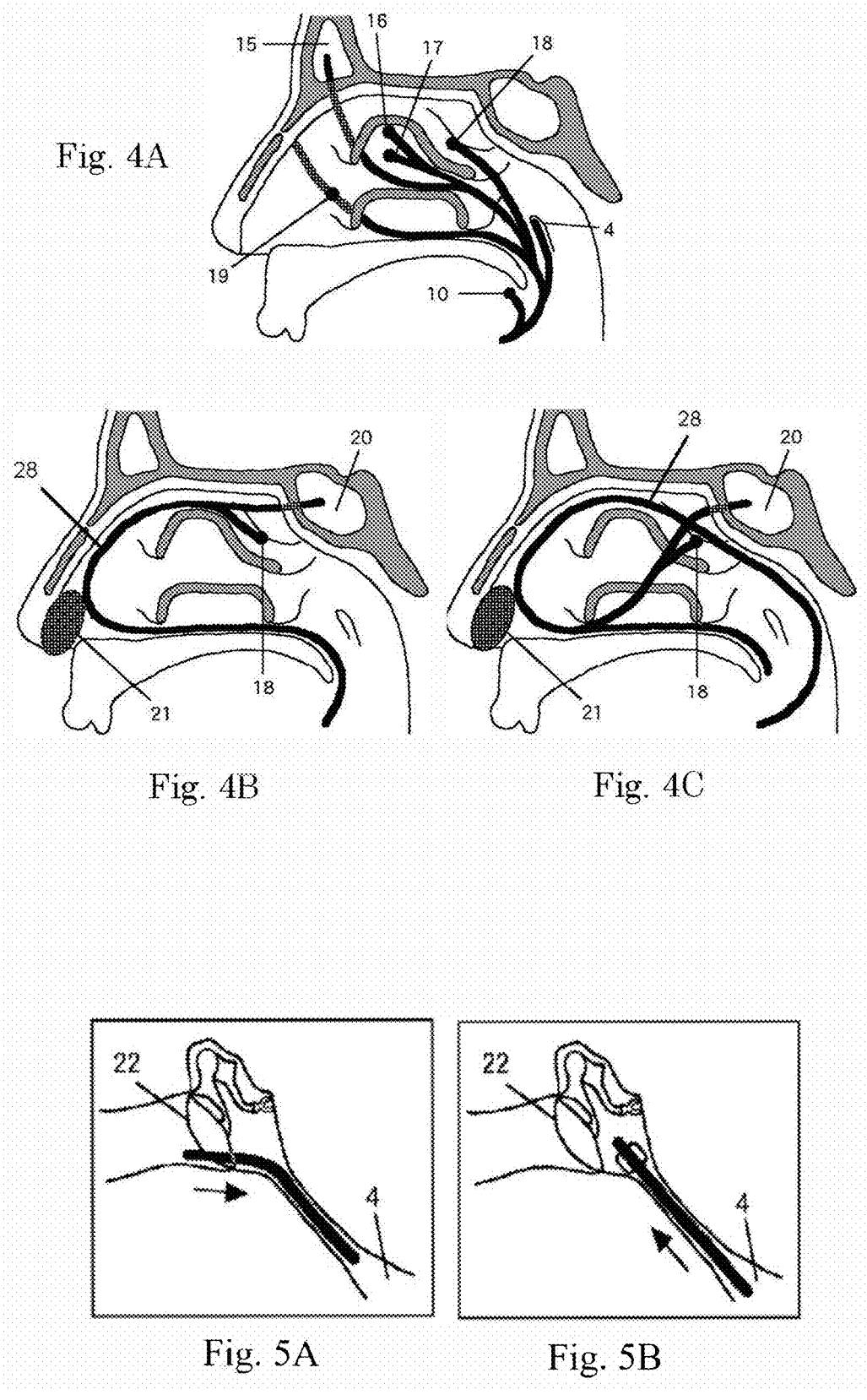

In the present invention, the Eustachian tube, aditus to mastoid antrum, maxillary sinus ostium, frontal sinus ostium, sphenoidal sinus ostium, ethmoidal sinus ostium, or nasolacrimal duct ostium can be dilated by using the balloon catheter, the high speed drill, or the laser catheter for securing the route of insertion (insertion route is shown in FIGS. 4(a), 4(b), and 4(c)), because these portions can be observed from the front. On the other hand, the dilation of these portions has not been performed in conventional endoscopic insertion method.

In the present invention, flexible endoscopic diagnosis can be performed in the Eustachian tube, tympanic cavity, mastoid antrum, maxillary sinus, frontal sinus, sphenoidal sinus, ethmoidal sinus, nasolacrimal duct, or lachrymal sac. Therefore, tumorectomy for the pathological diagnosis in these portions can be escaped.

In the present invention, the injecting tube can be readily inserted through the internal opening of second branchial cleft fistula around the tonsillar fossa by using the transorally inserted flexible endoscope for the treatment of second branchial cleft fistula (endoscopic transoral chemo-cauterization of second branchial cleft fistula), because the internal opening of second branchial cleft fistula can be observed from the front by the transorally inserted flexible endoscope. On the other hand, branchial fistulectomy has been performed in the conventional treatment.

In the present invention, a plug can be readily placed in the carniopharygeal canal by using the transorally inserted flexible endoscope for the treatment of persistent craniopharyngeal canal (endoscopic transoral transpharyngeal plug closure of craniopharyngeal canal), because the nasopharyngeal orifice of the carniopharygeal canal can be observed from the front by the transorally inserted flexible endoscope. On the other hand, transpalatal repair of basal skull base herniation has been performed in the conventional treatment.

In the present invention, a hemostatic procedure can be readily performed from the back by using the transorally inserted flexible endoscope for the treatment of posterior epistaxis which cannot be treated by using the transnasally inserted flexible endoscope (endoscopic transoral transpharyngeal hemostatic procedure for epistaxis), because the field of procedure can be broadened. On the other hand, transcatheter arterial embolization has been performed in the conventional treatment.

In the present invention, a plug can be readily placed by using the transorally inserted flexible endoscope for the treatment of skull base cerebrospinal fluid leak (endoscopic transoral transpharyngeal plug closure of skull base cerebrospinal fluid leak). On the other hand, surgery has been performed in the conventional treatment.

In the present invention, a plug can be readily placed by using the transorally and transpharyngeally inserted flexible endoscope for the treatment of oronasal fistula which is a complication of cleft palate surgery (endoscopic transoral transpharyngeal plug closure of the oronasal fistula), because the orifice of the oronasal fistula can be observed from the front by the transorally and transpharyngeally inserted flexible endoscope. On the other hand, conventionally used palatal obturator has occasionally induced dental caries and gingivitis and accidentally been swallowed.

In the present invention, the balloon catheter, the laser catheter and the drainage catheter can be readily inserted through the Eustachian tube into the mastoid antrum by using the transorally inserted flexible endoscope for the treatment of mastoiditis (endoscopic transoral transpharyngeal mastoid drainage), because the pharyngeal orifice of the Eustachian tube can be observed from the front by the transorally inserted flexible endoscope. On the other hand, mastoidectomy has been performed in the conventional treatment.

In the present invention, the cost can be reduced by using the transorally inserted flexible endoscope and balloon catheter for the treatment of sinusitis (endoscopic transoral transpharyngeal balloon sinus ostial dilation). On the other hand, the high cost is required due to the use of special devices (a special balloon catheter) in conventional balloon sinuplasty.

In the present invention, the balloon catheter can be readily inserted through the nasolacrimal duct ostium by using the transorally inserted flexible endoscope for the treatment of nasolacrimal duct obstruction (endoscopic transoral transpharyngeal balloon catheter dilation of the nasolacrimal duct), because the nasolacrimal duct ostium can be observed from the front by the transorally inserted flexible endoscope. On the other hand, there has been the risk of damaging the lachrymal punctum and the unsuccessful catheter insertion through the small lachrymal punctum in conventional transcanalicular balloon catheter dilation of nasolacrimal duct obstruction.

In the present invention, the probe can be readily inserted through the nasolacrimal duct ostium by using the transorally inserted flexible endoscope for the treatment of nasolacrimal duct obstruction (endoscopic transoral transpharyngeal nasolacrimal duct recanalization), because the nasolacrimal duct ostium can be observed from the front by the transorally inserted flexible endoscope. On the other hand, there has been the risk of damaging the lachrymal punctum and the unsuccessful catheter insertion through the small lachrymal punctum in conventional transcanalicular nasolacrimal duct recanalization.

In the present invention, the silicone stent can be readily inserted through the nasolacrimal duct ostium by using the transorally inserted flexible endoscope for the treatment of nasolacrimal duct obstruction (endoscopic transoral transpharyngeal nasolacrimal silicone stent intubation) (FIG. 6(b)), because the nasolacrimal duct ostium can be observed from the front by the transorally inserted flexible endoscope. On the other hand, there has been the risk of damaging the lachrymal punctum and the unsuccessful stent intubation through the small lachrymal punctum and the occurrence of a foreign body feeling in conventional transcanalicular nasolacrimal silicone stent intubation (FIG. 6(a)).

In the present invention, the metallic stent can be readily inserted through the nasolacrimal duct ostium by using the transorally inserted flexible endoscope for the treatment of nasolacrimal duct obstruction (endoscopic transoral transpharyngeal nasolacrimal metallic stent placement).

In the present invention, the balloon catheter can be readily inserted into of the Eustachian tube by using the transorally inserted flexible endoscope for the treatment of Eustachian tube dysfunction (endoscopic transoral transpharyngeal balloon Eustachian tuboplasty), because the pharyngeal orifice of the Eustachian tube can be observed from the front by the transorally inserted flexible endoscope. On the other hand, transnasal balloon catheter insertion has been performed in the conventional treatment.

Also, the laser catheter can be readily inserted into the Eustachian tube by using the transorally inserted flexible endoscope for the treatment of Eustachian tube dysfunction (endoscopic transoral transpharyngeal laser Eustachian tuboplasty), because the pharyngeal orifice of the Eustachian tube can be observed from the front by the transorally inserted flexible endoscope. On the other hand, transnasal laser catheter insertion has been performed in the conventional treatment.

In the present invention, injection into the torus tubarius can be readily performed by using the transorally inserted flexible endoscope for the treatment of patulous Eustachian tube (transoral endoscopic transoral injection into the torus tubarius), because the torus tubarius can be observed from the front by the transorally inserted flexible endoscope. On the other hand, transnasal endoscopic injection into the torus tubarius has been performed in the conventional treatment.

In the present invention, the catheter can be readily inserted into the Eustachian tube by using the transorally inserted flexible endoscope for the treatment of patulous Eustachian tube (endoscopic transoral transpharyngeal catheter insertion) (FIG. 5(b)), because the pharyngeal orifice of the Eustachian tube can be observed from the front by the transorally inserted flexible endoscope. On the other hand, surgical transtympanic catheter insertion has been performed in the conventional treatment (FIG. 5(a)).

In the present invention, routine check of the nasopharynx or nasal cavity can be performed in transoral flexible gastroscopy. On the other hand, the nasopharynx or nasal cavity have not been examined in conventional transoral flexible gastroscopy.

In the present invention, the obstructive disorder which prevents the transnasal flexible endoscope insertion can be diagnosed by using the transorally inserted flexible endoscope. On the other hand, when the transnasal flexible endoscope cannot be inserted, the obstructive disorder of the nasopharynx or nasal cavity has not been diagnosed in conventional transnasal flexible endoscopy.

In the present invention, the lateral wall of the hollow organs (hypopharynx, larynx, trachea, bronchus, bile duct, pancreatic duct, duodenum, stomach, esophagus, urethra, bladder, ureter, renal pelvis, vagina, uterus) can be observed from the front, because the hollow organs are rotated in relative terms by changing the body position to the semi-lateral position or the lateral position. On the other hand, the lateral wall of the hollow organs cannot be observed from the front in the sitting, semi-recumbent, supine, lithotomy, or prone position in conventional flexible endoscopy.

In the present invention, the endoscope insertion into branches which open in the lateral wall of the hollow organs (bronchus, pancreatic duct, bile duct), the endoscope insertion into the fallopian tube and the ureteral access sheath insertion can be readily performed, because the hollow organs are rotated in relative terms by changing the body position to the semilateral position or the lateral position. On the other hand, the endoscope insertion into branches which open in the lateral wall of the hollow organs, the endoscope insertion into the fallopian tube and the ureteral access sheath insertion cannot be occasionally performed in the sitting, semi-recumbent, supine, lithotomy, or prone position in conventional flexible endoscopy.

In the present invention, the retraction of the organs can be readily performed in a narrow space in which retractors or grasping forceps cannot be used in natural orifice transluminal endoscopic surgery (flexible endoscopic organ retraction method in natural orifice transluminal endoscopic surgery), because the organs are retracted with the flexible endoscope itself.

In the present invention, the retraction of the organs can be readily performed in a narrow space in which retractors or grasping forceps cannot be used in single-incision flexible endoscopic surgery (flexible endoscopic organ retraction method in single-incision flexible endoscopic surgery), because the organs are retracted with the flexible endoscope itself.

In the present invention, the flexible endoscopic tongue retraction method was devised for securing the broader operative field in the tonsillar fossa. This method reproduces the surgical retraction procedure with the left hand during laparotomy, and this method is applied to flexible endoscopic surgery for securing the broader operative field.

The flexible colonoscope insertion method invented by the applicant can be referred to paper published in the Gastrointestinal Endoscopy and the 2 unpublished papers posted on the preprint server.

Points of the flexible colonoscope insertion method are as follows.

1) The patient should be placed in the body position in which the entry site is highest and the exit site is lowest (left semiprone position for the sigmoid colon).
2) The flexed flexible colonoscope should be straightened by rotating the flexible colonoscope by 180 degrees or more (in the sigmoid colon, the flexed flexible colonoscope can be straightened by rotating the flexible colonoscope to the left by 180 degrees or more in the left semiprone position).
3) The flexure of the flexible colonoscope should be prevented by applying a torque and pressing the flexible colonoscope against the fixed organ (in the sigmoid colon, the flexure of the flexible colonoscope can be prevented by applying a torque to the left and pressing the flexible colonoscope against the retroperitoneum in the left semiprone position).

The applicant devised the present invention based on the above flexible colonoscope insertion method. The applied points are as follows.

1) Rotating of the hollow organ in relative terms by changing the body position to the semilateral or the lateral position for observing the lateral wall of the lumen.
2) Retracting the organ with the flexible endoscope itself by rotating the flexible endoscope in the counter direction of the lumen for securing the visual field (laterally retracting the torus tubarius, and medially retracting the tongue).
3) Making more larger looping of the flexible endoscope by rotating the flexible endoscope by 360 degrees in the counter direction of the lumen for directing the tip of the flexible endoscope to the pharyngeal orifice of the Eustachian tube.

Several exemplary device insertion methods are provided below. Exemplary Method 1 includes:

Step 1-(a): rotating a hollow organ by 45 to 135 degrees by changing a body position of a patient to a semilateral, lateral, or semiprone position for observing a lateral wall of a lumen of the hollow organ, wherein the body position was a supine, semi-recumbent, sitting, lithotripsy, or prone position, wherein if the patient is placed in the body position other than the semilateral, lateral, or semiprone position and the body position must be changed to the semilateral, lateral, or semiprone position during a procedure, the device is remain inserted, or the device is removed, the body position is changed, and the device is reinserted, and if it is known from a beginning of the procedure that the lateral wall of the lumen of the hollow organ will be observed, the patient is placed in the semilateral, lateral, or semiprone position at the beginning of the procedure.

Step 1-(b): inserting the device into a lumen while rotating a holding portion of the device clockwise or counterclockwise from the perspective of a person operating the device; turning a tip of the device to the lateral wall of the lumen counterclockwise after inserting the device while rotating the holding portion of the device clockwise, or clockwise after inserting the device while rotating the holding portion of the device counterclockwise; and examining the lateral wall of the lumen.

Step 1-(c): inserting the device into a lumen while rotating the holding portion of the device counterclockwise by 360 degrees from the perspective of a person operating the device, wherein the device forms a loop for avoiding contact with organs, securing the visual field or securing the insertion route.

Step 1-(d): retracting an organ inside the hollow organ with the device itself by rotating the holding portion of the device counterclockwise or clockwise from the perspective of the person operating the device for securing the visual field or securing the insertion route, wherein the device is rotated counterclockwise or clockwise while the device is not pulled to prevent the effect of retraction from weakening.

Step 1-(e): retracting the organ inside the hollow organ with the device itself by pulling or pushing the device while applying an upward angle for securing the visual field or securing the insertion route, wherein the device is pulled or pushed while the device is not rotated for preventing the effect of retraction from weakening. This means pushing the holding portion of the device, which causes the tip/end of the scope/device to move forward.

Step 1-(f): retracting the organ inside the hollow organ with the device itself by pushing the device while applying a downward angle for securing the visual field or securing the insertion route, wherein the device is pushed while the device is not rotated for preventing the effect of retraction from weakening.

An Exemplary Method 2 includes Exemplary Method 1 and further includes wherein the device is configured such that the organ can be readily retracted by increasing the stiffness, the friction coefficient, or the diameter of the device, wherein the device used in the method is selected from the group consisting of: a flexible endoscope, a tracheal tube, a ileus tube, and a gastric tube. In other words, the device is configured to increase the stiffness, the friction coefficient, or the diameter of the device.

An Exemplary Method 3 includes Exemplary Method 1 and further includes retracting the patient's tongue with the device itself for securing the insertion route, reducing gag reflex, and reducing sedatives, and the device forms a loop in the patient's oral cavity, oropharynx and hypopharynx, comprising the steps of: placing the patient in the left lateral or the left semiprone position; placing a mouthpiece in the patient's mouth; inserting the device through the mouthpiece into the oropharynx; rotating the device clockwise for positioning the device on a lateral side of the tongue; rotating the device counterclockwise for medially retracting the tongue with the device itself; and inserting the device through the side of the tongue into the patient's left pyriform sinus while rotating the device counterclockwise.

An Exemplary Method 4 includes Exemplary Method 1 and further includes retracting the patient's tongue with the device itself for securing the insertion route, reducing gag reflex, and reducing sedatives, and the device forms a loop in the patient's oral cavity, oropharynx and hypopharynx by rotating the device counterclockwise, wherein the device is not rotated clockwise, comprising the steps of: placing the patient in the left lateral or the left semiprone position; placing a mouthpiece in the patient's mouth; inserting the device through the mouthpiece along a lateral side of the tongue into the oropharynx while rotating the device counterclockwise; inserting the device along a lateral wall of the pharynx into the patient's left pyriform sinus while rotating the device counterclockwise.

An Exemplary Method 5 includes Exemplary Method 1 and further includes observing the patient's hypopharynx including the patient's right pyriform sinus, left pyriform sinus, postcricoid region and posterior wall of the hypopharynx.

An Exemplary Method 6 includes Exemplary Method 6 and further includes observing the right pyriform sinus, wherein the patient's tongue is retracted with the flexible endoscope itself, and the flexible endoscope forms a loop in the oral cavity; the oropharynx and the hypopharynx, comprising the steps of: placing the patient in the left lateral or the left semiprone position; placing a mouthpiece in the patient's mouth; inserting the flexible endoscope through the mouthpiece into the oropharynx; rotating the flexible endoscope clockwise for positioning the flexible endoscope on a lateral side of the tongue; rotating the flexible endoscope counterclockwise for medially retracting the tongue with the flexible endoscope itself; inserting the flexible endoscope through the side of the tongue into the left pyriform sinus while rotating the flexible endoscope counterclockwise; turning the tip of the flexible endoscope to the right pyriform sinus by rotating the flexible endoscope clockwise by 90 degrees so as to observe the patient's glottis in the 9 o'clock position; inserting the flexible endoscope into the right pyriform sinus; and examining the right pyriform sinus.

An Exemplary Method 7 includes Exemplary Method 6 and further includes observing the postcricoid region and the posterior wall of the hypopharynx, wherein the patient's tongue and the cricoid cartilage are retracted with the flexible endoscope itself, and the flexible endoscope forms a loop in the oral cavity; the oropharynx and the hypopharynx, comprising the steps of: placing the patient in the left lateral or the left semiprone position; placing a mouthpiece in the patient's mouth; inserting the flexible endoscope through the mouthpiece into the oropharynx; rotating the flexible endoscope clockwise for positioning the flexible endoscope on a lateral side of the tongue; rotating the flexible endoscope counterclockwise for medially retracting the tongue with the flexible endoscope itself; inserting the flexible endoscope through the side of the tongue into the left pyriform sinus while rotating the flexible endoscope counterclockwise; inserting the flexible endoscope into the esophagus while rotating the flexible endoscope counterclockwise or clockwise; rotating the flexible endoscope clockwise or counterclockwise so as to observe the anterior wall of the esophagus in the 9 o'clock position;

pulling the flexible endoscope while applying an upward angle for anteriorly retracting the cricoid cartilage; inserting the flexible endoscope between the cricoid cartilage and the posterior wall of the hypopharynx; examining the postcricoid region and the posterior wall of the hypopharynx; removing the flexible endoscope into the left pyriform sinus while rotating the flexible endoscope counterclockwise; examining the left pyriform sinus; inserting the flexible endoscope into the right pyriform sinus while rotating the flexible endoscope clockwise and applying an upward angle; examining the right pyriform sinus; pushing the flexible endoscope while applying a downward angle for anteriorly retracting the cricoid cartilage; inserting the flexible endoscope between the cricoid cartilage and the posterior wall of the hypopharynx; examining the postcricoid region and the posterior wall of the hypopharynx; removing the flexible endoscope into the left pyriform sinus while rotating the flexible endoscope counterclockwise; pushing the flexible endoscope while applying an upward angle for anteriorly retracting the cricoid cartilage; inserting the flexible endoscope between the cricoid cartilage and the posterior wall of the hypopharynx; and examining the postcricoid region and the posterior wall of the hypopharynx.

An Exemplary Method 8 includes Exemplary Method 1 and further includes inserting the tracheal tube in the left lateral or the left semiprone position, wherein the patient's tongue is retracted with the tracheal tube itself, and the tracheal tube forms a loop in the patient's oral cavity, oropharynx and hypopharynx, comprising the steps of: attaching the flexible endoscope inside the tracheal tube; placing the patient in the left lateral or the left semiprone position; placing a mouthpiece in the patient's mouth; inserting the tracheal tube through the mouthpiece into the oropharynx; rotating the tracheal tube clockwise for positioning the tracheal tube on a lateral side of the tongue; rotating the tracheal tube counterclockwise for medially retracting the tongue with the tracheal tube itself; inserting the tracheal tube through the side of the tongue into the patient's left pyriform sinus while rotating the tracheal tube counterclockwise; turning the tip of the tracheal tube to the patient's glottis by rotating the tracheal tube clockwise by 90 degrees so as to observe the glottis in the 9 o'clock position; inserting the tracheal tube into the patient's trachea while rotating the tracheal tube counterclockwise; detaching the flexible endoscope from the tracheal tube; and confirming the tracheal tube insertion by cough reflex or respiratory sound.

An Exemplary Method 9 includes Exemplary Method 9 and further includes inserting the tracheal tube with the flexible endoscope is not attached, wherein the tracheal tube can be inserted when the visual field cannot be secured due to bleeding, tumor, injury, or foreign body.

An Exemplary Method 10 includes Exemplary Method 1 and further includes inserting the flexible gastroscope through the patient's left pyriform sinus, wherein the patient's tongue is retracted with the flexible gastroscope itself, and the flexible gastroscope forms a loop in the patient's oral cavity, oropharynx and hypopharynx, comprising the steps of: placing the patient in the left lateral or the left semiprone position; placing a mouthpiece in the patient's mouth; inserting the flexible gastroscope through the mouthpiece into the oropharynx; rotating the flexible gastroscope clockwise for positioning the flexible gastroscope on a lateral side of the tongue; rotating the flexible gastroscope counterclockwise for medially retracting the tongue with the flexible gastroscope itself; inserting the flexible gastroscope through the side of the tongue into the left pyriform sinus while rotating the flexible gastroscope counterclockwise; and inserting the flexible gastroscope into the esophagus while rotating the flexible gastroscope counterclockwise or clockwise.

An Exemplary Method 11 includes Exemplary Method 1 and further includes inserting the flexible gastroscope through the patient's right pyriform sinus, wherein the patient's tongue is retracted with the flexible gastroscope itself, and the flexible gastroscope forms a loop in the patient's oral cavity; oropharynx and hypopharynx, comprising the steps of: placing the patient in the left lateral or the left semiprone position; placing a mouthpiece in the patient's mouth; inserting the flexible gastroscope through the mouthpiece into the oropharynx; rotating the flexible gastroscope clockwise for positioning the flexible gastroscope on a lateral side of the tongue; rotating the flexible gastroscope counterclockwise for medially retracting the tongue with the flexible gastroscope itself; inserting the flexible gastroscope through the side of the tongue into the patient's left pyriform sinus while rotating the flexible gastroscope counterclockwise; turning the tip of the flexible gastroscope to the right pyriform sinus by rotating the flexible gastroscope clockwise by 90 degrees so as to observe the patient's glottis in the 9 o'clock position; inserting the flexible gastroscope into the right pyriform sinus while rotating the flexible gastroscope clockwise by 90 degrees; and inserting the flexible gastroscope into the esophagus while rotating the flexible gastroscope clockwise.

An Exemplary Method 12 includes a flexible endoscope insertion method, comprising:

Step 12-(a): rotating a body cavity by 0 to 90 degrees by changing a patient's body position to a desired position for observing a lateral side of an organ in the body cavity, wherein if the body position must be changed during a procedure, the flexible endoscope is remain inserted, or the flexible endoscope is removed, the body position is changed, and the flexible endoscope is reinserted, and if it is known from a beginning of the procedure that the lateral side of the organ in the body cavity will be observed, the patient is placed in the desired position at the beginning of the procedure.

Step 12-(b): inserting the flexible endoscope toward the organ while rotating an insertion portion of the flexible endoscope clockwise or counterclockwise from the perspective of a person operating the flexible endoscope; turning a tip of the flexible endoscope to the lateral side of the organ by rotating the insertion portion of the flexible endoscope counterclockwise after inserting the flexible endoscope while rotating the insertion portion of the flexible endoscope clockwise, or rotating the insertion portion of the flexible endoscope clockwise after inserting the flexible endoscope while rotating the insertion portion of the flexible endoscope counterclockwise; and examining the lateral side of the organ.

Step 12-(c): inserting the flexible endoscope toward the organ inside the body cavity while rotating the insertion portion of the flexible endoscope counterclockwise by 360 degrees from the perspective of a person operating the flexible endoscope, wherein the flexible endoscope forms a loop for avoiding contact with organs, securing the visual field or securing the insertion route.

Step 12-(d): retracting an organ inside the body cavity with the flexible endoscope itself by rotating the insertion portion of the flexible endoscope counterclockwise or clockwise from the perspective of the person operating the endoscope for securing the visual field or securing the insertion route, wherein the flexible endoscope is rotated counterclockwise or clockwise while the flexible endoscope is not pulled to prevent the effect of retraction from weakening.

Step 12-(e): retracting an organ inside the body cavity with the flexible endoscope itself by pulling or pushing the flexible endoscope while applying an upward angle for securing the visual field or securing the insertion route, wherein the flexible endoscope is pulled or pushed while the flexible endoscope is not rotated to prevent the effect of retraction from weakening.

Step 12-(f): retracting an organ inside the body cavity with the flexible endoscope itself by pushing the flexible endoscope while applying a downward angle for securing the visual field or securing the insertion route, wherein the flexible endoscope is pushed while the flexible endoscope is not rotated to prevent the effect of retraction from weakening.

An Exemplary Method 13 includes Exemplary Method 12, further including wherein the flexible endoscope is configured such that the organ can be readily retracted by increasing the stiffness, the friction coefficient, or the diameter of the insertion portion of the flexible endoscope.

An Exemplary Method 14 includes Exemplary Method 12 and further includes a natural orifice transluminal cholecystectomy, wherein the patient's duodenum, transverse colon, and greater omentum is retracted with the flexible endoscope itself, comprising the steps of: inserting the flexible endoscope through the patient's anus into the patient's large intestine; projecting the device from the tip of the flexible endoscope; incising a wall of the large intestine; inserting the flexible endoscope through the wall of the large intestine into an abdominal cavity; inserting the flexible endoscope around the patient's distended common bile duct; turning the tip of the flexible endoscope to a right lateral side of the common bile duct by rotating the flexible endoscope counterclockwise, and simultaneously, medially and inferiorly retracting the duodenum, transverse colon, and greater omentum with the flexible endoscope itself by rotating the flexible endoscope counterclockwise for securing the broader operative field; exposing a cystic duct and cystic artery in a right lateral side of the distended common bile duct; ligating and incising the cystic duct and cystic artery; and resecting the patient's gallbladder.

In the present invention, as stated in Exemplary Method 1, step 1-(a) above, a body position is changed to a semi-lateral, lateral, or semiprone position for observing a lateral wall of a lumen of the hollow organ. If the patient is placed in the body position other than the semilateral, lateral, or semiprone position and the body position must be changed to the semilateral, lateral, or semiprone position during procedure, the device is remain inserted, or the device is removed, the body position is changed, and the device is reinserted, and if it is known from the beginning that the lateral wall of the lumen of the hollow organ will be observed, the patient is placed in the semilateral, lateral, or semiprone position at the beginning of the procedure.

In the present invention, as stated in step 1-(c) and Exemplary Method 11, the device is inserted into the lumen while rotating the device counterclockwise by 360 degrees from the perspective of a person operating the device, wherein the device forms a loop for avoiding contact with organs, securing the visual field or securing the insertion route.

In the present invention, as stated in step 1-(d), the device is rotated counterclockwise or clockwise for retracting the organ inside the hollow organ while the device is not pulled for preventing the effect of retraction from weakening. If the device is rotated while the device is pulled, the organ cannot be retracted.

In the present invention, as stated in step 1-(e), the device is pulled or pushed while applying an upward angle for retracting the organ inside the hollow organ while the device is not rotated for preventing the effect of retraction from weakening. If the device is pulled or pushed while the device is rotated, the organ cannot be retracted.

In the present invention, as stated in step 1-(f), the device is pushed while applying a downward angle for retracting the organ inside the hollow organ while the device is not rotated for preventing the effect of retraction from weakening. If the device is pushed while the device is rotated, the organ cannot be retracted.

In the present invention, as stated in Exemplary Method 2 above, the device is configured such that the organ can be readily retracted by increasing the stiffness, the friction coefficient, or the diameter of the device. On the other hand, the organ could not be retracted with the device itself, because the soft, thin device with low friction coefficient has been used in conventional insertion method.

In the present invention, as stated in Exemplary Method 2, the flexible endoscope, the tracheal tube, the ileus tube, the gastric tube can be used, but are not restricted to them.

In the present invention, the device is inserted through the mouthpiece. It is preferable that the mouthpiece has a same cylindrical shape as the mouthpiece used in gastroscopy, and it is more preferable that the mouthpiece has a wide width and an elliptical shape so that the device can be moved with ease.

In the present invention, the retracted tongue can be seen as a bump on the right side of the visual field in the oropharynx and the hypopharynx, because the device is inserted through the side of the retracted tongue.

In the present invention, if the patient is placed in the left semiprone position, the tongue can be retracted more securely compared to when the patient is placed in the left lateral position, because the oral cavity and the oropharynx are rotated by 45 degrees from the perspective of the person operating the device.

In the present invention, as stated in Exemplary Method 4, if the device is inserted through the mouthpiece along the lateral side of the tongue, the tongue can be retracted more securely compared to the method described in Exemplary Method 3. In that case, more large loop is formed in the oral cavity, the oropharynx and the hypopharynx compared to the method described in Exemplary Method 3.

In the present invention, as stated in Exemplary Method 6, the lateral wall of the hollow organ (the pyriform sinus of the hypopharynx) can be observed from the front, because the hollow organ (hypopharynx) is rotated in relative terms by changing the body position to the lateral or semiprone position. On the other hand, the lateral wall of the hollow organ (the pyriform sinus of the hypopharynx) cannot be observed from the front in the sitting or supine position in conventional flexible endoscopy.

In the present invention, as stated in Exemplary Method 7, the postcricoid region and the posterior wall of the hypopharynx can be observed, because the cricoid cartilage is anteriorly retracted with the flexible endoscope itself. On the other hand, the postcricoid region and the posterior wall of the hypopharynx cannot be observed in conventional flexible endoscopy.

In the present invention, when the cricoid cartilage is anteriorly retracted, the entrance of the esophagus becomes bean-shaped, because the cricoid cartilage compresses the anterior wall of the entrance of the esophagus.

In the present invention, when the cricoid cartilage is anteriorly retracted, a vertical fold develops on the anterior wall the esophagus.

In the present invention, if the flexible endoscope is positioned just right to retract the cricoid cartilage, either the left pyriform sinus or right pyriform sinus, postcricoid region, posterior wall of the hypopharynx and entrance of the esophagus can be captured simultaneously in one image, and these parts can be observed seamlessly. On the other hand, only fragmentary images were obtained in conventional flexible endoscopy.

The applicant has devised the tracheal tube insertion method based on the flexible gastroscope insertion method devised in the present invention. The method of operating the tracheal tube is the same as the method of operating the flexible gastroscope. The feature is that the tracheal tube, which was conventionally inserted in the supine position, can be inserted in the left lateral or the left semiprone position.

In the present invention, even if there is trismus, if the mouthpiece can be placed in the mouth, the tracheal tube can be inserted through the mouthpiece into the trachea while a laryngoscope blade is not used. On the other hand, the mouth must be opened wider enough to insert the laryngoscope blade in conventional insertion method.

In the present invention, even if there is a oral tumor, tongue tumor, tonsil enlargement, oropharyngeal tumor, hypopharyngeal tumor, or thyroid tumor, the tracheal tube can be inserted into the trachea if there is space for the tracheal tube to pass through. On the other hand, unless there is space for the laryngoscope blade to insert, space to secure the field of view, and space for the tracheal tube to pass through, the tracheal tube could not be inserted into the trachea in conventional insertion method.

In the present invention, the tracheal tube can be inserted into the trachea without laryngeal expansion. On the other hand, there has been a risk of hypertension, tachycardia, or vagal reflex due to laryngeal expansion in conventional insertion method.

In the present invention, the tracheal tube can be inserted into the trachea without the risk of esophageal intubation. On the other hand, there has been a risk of hypoxemia due to esophageal intubation in conventional insertion method.

In the present invention, the tracheal tube can be inserted into the trachea without the risk of aspiration, because vomit is excreted through the mouth. On the other hand, there has been a risk of aspiration in the supine position in conventional insertion method.

In the present invention, when performing general anesthesia, tracheal tube can be inserted without muscle relaxant administration and mask ventilation. On the other hand, there has been a risk of hypoxemia due to mask ventilation failure after administration of muscle relaxants in conventional insertion method.

In the present invention, when the visual field cannot be secured due to bleeding, tumor, injury, or foreign body, the tracheal tube can be inserted blindly and the tracheal tube insertion can be confirmed by cough reflex or respiratory sound.

In the present invention, gag reflex can be weakened and the amount of sedatives can be reduced in transoral gastroscopy, because the tongue is medially retracted with the flexible gastroscope itself and the base of the tongue is not stimulated as much by the flexible gastroscope. On the other hand, there has been pain, hypertension, or tachycardia due to gag reflex, respiratory depression, hypotension, or bradycardia due to sedatives in conventional insertion method.

In the present invention, gag reflex can be weakened and the amount of sedatives can be reduced in transoral gastroscopy, because the flexible gastroscope forms a loop in the oral cavity, the oropharynx and the hypopharynx by rotating the insertion portion of the flexible gastroscope counterclockwise and the base of the tongue is not stimulated as much by the flexible gastroscope. On the other hand, there has been pain, hypertension, or tachycardia due to gag reflex, respiratory depression, hypotension, or bradycardia due to sedatives in conventional insertion method.

The applicant has devised the method for inserting the transoral flexible gastroscope through the right pyriform sinus. The transoral flexible gastroscope can be more easily inserted through the right pyriform sinus than through the left pyriform sinus. In fact, if the patient is not sedated and cannot swallow the flexible gastroscope, the flexible gastroscope is automatically rotated clockwise by the force of the pharyngeal muscles for swallowing and the tip of the flexible gastroscope is directed to the right pyriform sinus and the flexible gastroscope readily inserted through the right pyriform sinus.

In the present invention, as stated in Exemplary Method 12, step 12-(a), a body position is changed to a desired position for observing a lateral side of an organ in the body cavity. If the body position must be changed during procedure, the flexible endoscope is remain inserted (or the flexible endoscope is removed, the body position is changed, and the flexible endoscope is reinserted), and if it is known from the beginning that the lateral side of the organ in the body cavity will be observed, the patient is placed in the desired position at the beginning of the procedure.

In the present invention, as stated in step 12-(c), the flexible endoscope is inserted toward the organ inside the body cavity while rotating the insertion portion of the flexible endoscope counterclockwise by 360 degrees from the perspective of a person operating the flexible endoscope, wherein the flexible endoscope forms a loop for avoiding contact with organs, securing the visual field or securing the insertion route.

In the present invention, as stated in step 12-(d), the insertion portion of the flexible endoscope is rotated counterclockwise or clockwise for retracting the organ inside the body cavity while the flexible endoscope is not pulled for preventing the effect of retraction from weakening. If the flexible endoscope is rotated while the flexible endoscope is pulled, the organ can not be retracted.

In the present invention, as stated in step 12-(e), the flexible endoscope is pulled or pushed while applying an upward angle for retracting the organ inside the body cavity while the flexible endoscope is not rotated to prevent the effect of retraction from weakening. If the flexible endoscope is pulled or pushed while the flexible endoscope is rotated, the organ cannot be retracted.

In the present invention, as stated in step 12-(f), the flexible endoscope is pushed while applying a downward angle for retracting the organ inside the body cavity while the flexible endoscope is not rotated to prevent the effect of retraction from weakening. If the flexible endoscope is pushed while the flexible endoscope is rotated, the organ cannot be retracted.

In the present invention, as stated in Exemplary Method 13, the flexible endoscope is configured such that the organ can be readily retracted by increasing the stiffness, the friction coefficient, or the diameter of the flexible endoscope. On the other hand, the organ could not be retracted with the flexible endoscope itself, because the soft, thin flexible endoscope with low friction coefficient has been used in conventional insertion method.

In the following section, specific examples of implementation are described, but the present invention is not restricted by these examples, and substitutions and improvements usually made by those skilled in the art are included in the invention.

Example 1

Flexible endoscope insertion method into the nasopharynx and the nasal cavity; lidocaine viscous 2% is implemented by several times by 1 ml at 1-minute intervals and the patient swallow it, and a sedative drug is administered. The patient is placed in the left lateral position. The gastroscope is inserted through the mouth, and the esophagus, stomach, duodenum, and hypopharynx are examined, and when the tip of the gastroscope has reached the oropharynx, the gastroscope is inserted into the nasopharynx by gradually rotating the gastroscope to the right and simultaneously gradually applying an upward angle while maintaining a slight distance between the gastroscope and the posterior pharyngeal wall and slightly pushing the gastroscope, and the nasopharynx is examined.

Also, when a beginner performs this operation, the gastroscope may be inserted into the nasopharynx by rotating the gastroscope to the right so as to be observed the palatine uvula in the direction of 3 o'clock, and further rotating the gastroscope to the right while applying an upward angle, and slightly pushing the gastroscope.

When the sedative drug is not effective, since muscles of the nasopharynx are contracted, the examination of the nasopharynx is difficult.

Here, the anesthetic is sprayed over an area of 15-25 mm in diameter from a distance of 15-20 mm by using a tube projected from the gastroscope. The gastroscope is inserted into the pharyngonasal junction by pushing the gastroscope, and the pharyngonasal junction is examined.

Because the pharyngonasal junction is hard, the gastroscope cannot be occasionally inserted into the pharyngonasal junction. At this time, if the gastroscope is continued to be pushed without rotating the gastroscope, the gastroscope may suddenly advance and stimulate the pharyngonasal junction. Therefore, the gastroscope should be advanced while rotating to the left or right. Also, if the gastroscope is advanced to a dead end in the pharyngonasal junction, rotation of the gastroscope becomes difficult and the visual field is narrowed. At this time, if the gastroscope is forced to be rotated, the gastroscope may stimulate the pharyngonasal junction. Therefore, the gastroscope should not be advanced to a dead end in the pharyngonasal junction.

Here, the anesthetic is sprayed over an area of 15-25 mm in diameter from a distance of 15-20 mm by using a tube projected from the gastroscope. The gastroscope is inserted into the nasal cavity by pushing the gastroscope, and the nasal cavity is examined.

Example 2

Flexible endoscope insertion method into the pharyngeal orifice of the right Eustachian tube (FIG. 8): the patient is placed in the left lateral position. As shown in the figure, the white shaded portion of the gastroscope is inserted into the nasopharynx (see also, FIG. 11). The gastroscope is inserted through the mouth into the oropharynx, and the gastroscope is inserted into the nasopharynx by gradually rotating the gastroscope to the right and simultaneously gradually applying an upward angle while maintaining a slight distance between the gastroscope and the posterior pharyngeal wall and slightly pushing the gastroscope, and the tip of the gastroscope is turned to the pharyngeal orifice of the right Eustachian tube by rotating the gastroscope to the left, and the pharyngeal orifice of the right Eustachian tube is examined.

Example 3

Flexible endoscope insertion method into the pharyngeal orifice of the right Eustachian tube by making the more larger looping of the endoscope: the patient is placed in the left lateral position. The gastroscope is inserted through the mouth into the oropharynx, and the tip of the gastroscope is turned to the left by rotating the gastroscope to the left by 90 degrees, and the tip of the gastroscope is turned furthermore to the left by rotating the gastroscope to the left by 180 degrees, and the gastroscope is inserted into the nasopharynx while rotating the gastroscope to the left by 90 degrees, and the tip of the gastroscope is directed to the right lateral wall of the nasopharynx, and the pharyngeal orifice of the right Eustachian tube is examined.

Also, when a beginner performs this operation, the gastroscope may be rotated to the left in the oropharynx so as to be observed the palatine uvula in the direction of 6 o'clock, and the gastroscope is applied a downward angle, and the gastroscope is inserted while further rotating the gastroscope to the left.

Example 4

Flexible endoscope insertion method into the right Rosenmüller's fossa (FIG. 11): the patient is placed in the left semilateral position. The gastroscope 28 is inserted through the mouth into the oropharynx, and the gastroscope is inserted into the nasopharynx by gradually rotating the gastroscope to the right and simultaneously gradually applying an upward angle while maintaining a slight distance between the gastroscope and the posterior pharyngeal wall and slightly pushing the gastroscope. In the nasopharynx, the tip of the gastroscope is turned to the right Rosenmüller's fossa ostium medial to the pharyngeal orifice of the right Eustachian tube by rotating the gastroscope to the left, and the gastroscope is inserted into the right Rosenmüller's fossa 34 while laterally retracting the right torus tubarius 3 with the gastroscope itself, and the right Rosenmüller's fossa is examined.

When the sedative drug is not effective, since muscles of the nasopharynx are contracted, the Rosenmüller's fossa becomes hollow, or the orifice of the Rosenmüller's fossa and the Rosenmüller's fossa become slit-like, and examination of the Rosenmüller's fossa is difficult.

Example 5

Flexible endoscope insertion method into the right tonsillar fossa (FIG. 9): the patient is placed in the left lateral position. The gastroscope is inserted through the mouth into the oropharynx, and the gastroscope is rotated to the right so as to be observed the palatine uvula in the direction of 12 o'clock for positioning the gastroscope on the lateral side of the tongue, and the gastroscope is gradually rotated to the left while maintaining a slight distance between the gastroscope and the right posterior palatine arch for medially retracting the tongue with the gastroscope itself, and the gastroscope is inserted into the right tonsillar fossa by slightly pushing the gastroscope, and the right tonsillar fossa is examined.

If the tongue cannot be retracted medially, the tongue can be retracted medially by repeatedly rotating the gastroscope to the right or left until the fold becomes observable between the tongue and palatine tonsil.

Further, the gastroscope is inserted into the behind area of the right anterior palatine arch by slightly pushing the gastroscope, and the behind area of the right anterior palatine arch is examined. When the muscles of the tongue are relaxed by using the sedative drug, the tongue retraction is easy.

Example 6

Flexible endoscope insertion method into the left lateral palatine region, the left maxillary linguogingival region and the incisive papilla region 32 (FIG. 10): the patient is placed in the left lateral position. The gastroscope 28 is inserted through the mouth into the oral cavity; and the gastroscope is rotated to the left so as to be observed the median palatine suture 29 in the direction of 6 o'clock, and the tip of the gastroscope is turned to the left lateral palatine region 31 and the left maxillary linguogingival region 30 by rotating the gastroscope further to the left, and the gastroscope is inserted into the left lateral palatine region and the left maxillary linguogingival region by slightly pushing the gastroscope, and the left lateral palatine region and the left maxillary linguogingival region are examined.

And the tip of the gastroscope is turned to the incisive papilla region by rotating the gastroscope further to the left, and the gastroscope is inserted into the incisive papilla region by slightly pushing the gastroscope, and the incisive papilla region is examined.

Example 7

Flexible endoscope insertion method into the right tympanic cavity and the right mastoid antrum: the patient is placed in the left lateral position. The flexible endoscope is inserted through the mouth into the oropharynx, and the flexible endoscope is inserted into the nasopharynx by gradually rotating the flexible endoscope to the right and simultaneously gradually applying an upward angle while maintaining a slight distance between the flexible endoscope and the posterior pharyngeal wall and slightly pushing the flexible endoscope. In the nasopharynx, the tip of the flexible endoscope is turned to the pharyngeal orifice of the right Eustachian tube by rotating the flexible endoscope to the left, and the right Eustachian tube is dilated by using a balloon catheter, drill, and laser catheter, and the flexible endoscope is inserted into the right Eustachian tube and right tympanic cavity by pushing the flexible endoscope, and the right Eustachian tube and right tympanic cavity is examined, and the aditus to the right mastoid antrum is dilated by using a balloon catheter, drill, and laser catheter, and the flexible endoscope is inserted into the right mastoid antrum by pushing the flexible endoscope, and the right mastoid antrum is examined.

Example 8

Flexible endoscope insertion method into the craniopharyngeal canal: the patient is placed in the left lateral position. The flexible endoscope is inserted through the mouth into the nasopharynx, and the nasopharyngeal wall around the nasopharyngeal orifice of the craniopharyngeal canal is incised, and the nasopharyngeal orifice of the craniopharyngeal canal is exposed, and the flexible endoscope is inserted into the craniopharyngeal canal by pushing the flexible endoscope, and the craniopharyngeal canal is examined

Example 9

Flexible endoscope insertion method into the right maxillary sinus: the patient is placed in the left lateral position. The flexible endoscope is inserted through the mouth into the oropharynx, nasopharynx, and the right nasal cavity, and the right nasal cavity is examined, and the right maxillary sinus ostium is observed from the front, and the right maxillary sinus ostium is dilated by using a balloon catheter, drill, and laser catheter, and the flexible endoscope is inserted into the right maxillary sinus by pushing the flexible endoscope, and the right maxillary sinus is examined.

Example 10

Flexible endoscope insertion method into the right anterior ethmoidal sinus: the patient is placed in the left lateral position. The flexible endoscope is inserted through the mouth into the oropharynx, nasopharynx, and the right nasal cavity, and the right nasal cavity is examined, and the right anterior ethmoidal sinus ostium is observed from the front, and the right anterior ethmoidal sinus ostium is dilated by using a balloon catheter, drill, and laser catheter, and the flexible endoscope is inserted into the right anterior ethmoidal sinus by pushing the flexible endoscope, and the right anterior ethmoidal sinus is examined.

Example 11

Flexible endoscope insertion method into the right frontal sinus: the patient is placed in the left lateral position. The flexible endoscope is inserted through the mouth into the oropharynx, nasopharynx, and the right nasal cavity, and the right nasal cavity is examined, and the right frontal sinus ostium is observed from the front, and the right frontal sinus ostium is dilated by using a balloon catheter, drill, and laser catheter, and the flexible endoscope is inserted into the right frontal sinus by pushing the flexible endoscope, and the right frontal sinus is examined.

Example 12

Flexible endoscope insertion method into the right nasolacrimal duct and right lachrymal sac: the patient is placed in the left lateral position. The flexible endoscope is inserted through the mouth into the oropharynx, nasopharynx, and the right nasal cavity, and the right nasal cavity is examined, and the right nasolacrimal duct ostium is dilated by using a balloon catheter, drill, and laser catheter, and the flexible endoscope is inserted into the right nasolacrimal duct and right lachrymal sac by pushing the flexible endoscope, and the right nasolacrimal duct and right lachrymal sac is examined.

Example 13

Flexible endoscope insertion method into the right sphenoidal sinus: the patient is placed in the left lateral position. The flexible endoscope is inserted through the mouth into the oropharynx, nasopharynx, and the right nasal cavity, and the right nasal cavity is examined, and a loop of the flexible endoscope is made by applying a nasal plug and pushing the flexible endoscope, and the right sphenoidal sinus ostium is observed from the front, and the right sphenoidal sinus ostium is dilated by using a balloon catheter, drill, and laser catheter, and the flexible endoscope is inserted into the right sphenoidal sinus by pushing the flexible endoscope, and the right sphenoidal sinus is examined.

Example 14

Flexible endoscope insertion method into the right posterior ethmoidal sinus: the patient is placed in the left lateral position. The flexible endoscope is inserted through the mouth into the oropharynx, nasopharynx, and the right nasal cavity, and the right nasal cavity is examined, and a loop of the flexible endoscope is made by applying a nasal plug and pushing the flexible endoscope, or the loop of the flexible endoscope is not made, and the right posterior ethmoidal sinus ostium is observed from the front, and the right posterior ethmoidal sinus ostium is dilated by using a balloon catheter, drill, and laser catheter, and the flexible endoscope is inserted into the right posterior ethmoidal sinus by pushing the flexible endoscope, and the right posterior ethmoidal sinus is examined.

Example 15

Flexible endoscope insertion method into the anterior nasopharyngeal wall: the patient is placed in the left lateral position. The flexible endoscope is inserted through the mouth into the oropharynx, nasopharynx, and the right nasal cavity, and the right nasal cavity is examined, and a loop of the flexible endoscope is made by applying a nasal plug and pushing the flexible endoscope, and the flexible endoscope is re-inserted into the nasopharynx by pushing the flexible endoscope, and the anterior nasopharyngeal wall is observed from the front, and the anterior nasopharyngeal wall is examined.

Example 16

Natural orifice transluminal cholecystectomy: the flexible endoscope is inserted through the anus into the large intestine, and the device is projected from the flexible endoscope, and the wall of the large intestine is incised, and the flexible endoscope is inserted into the abdominal cavity. Then, the flexible endoscope is inserted around the common bile duct, and the tip of the flexible endoscope is turned to the right lateral side of the common bile duct by rotating the flexible endoscope to the left, and simultaneously the duodenum, transverse colon, and greater omentum are medially and inferiorly retracted with the flexible endoscope itself by rotating the flexible endoscope to the left for securing the broader operative field (flexible endoscopic duodeno-co-lono-omental retraction method) (FIG. 7). Then, the cystic duct and cystic artery are exposed in the right lateral side of the distended common bile duct, and the cystic duct and cystic artery are ligated and incised, and the gallbladder is resected.

Example 17

Single-incision flexible endoscopic cholecystectomy: the abdominal wall is incised, and a port is established in the abdominal incision, and the flexible endoscope is inserted through the port into the abdominal cavity. Then, the flexible endoscope is inserted around the common bile duct, and the tip of the flexible endoscope is turned to the right lateral side of the common bile duct by rotating the flexible endoscope to the left, and simultaneously the duodenum, transverse colon, and greater omentum are medially and inferiorly retracted with the flexible endoscope itself by rotating the flexible endoscope to the left for securing the broader operative field (flexible endoscopic duodeno-colono-omental retraction method) (FIG. 7). Then, the cystic duct and cystic artery are exposed in the right lateral side of the distended common bile duct, and the cystic duct and cystic artery are ligated and incised, and the gallbladder is resected.

Example 18

Flexible endoscope insertion method into the right pyriform sinus (FIG. 12): the patient is placed in the left lateral or the left semiprone position. The mouthpiece is placed in the mouth. The gastroscope 28 is inserted through the mouthpiece into the oropharynx, and the gastroscope is rotated clockwise for positioning the gastroscope on the lateral side of the tongue 12, and the gastroscope is rotated counterclockwise for medially retracting the tongue with the gastroscope itself, and the gastroscope is inserted through the side of the tongue into the left pyriform sinus 35 while rotating the gastroscope counterclockwise, and the tip of the gastroscope is turned to the right pyriform sinus 36 by rotating the gastroscope clockwise by 90 degrees so as to observe the glottis in the 9 o'clock position, and the gastroscope is inserted into the right pyriform sinus, and the right pyriform sinus is examined.

Example 19

Flexible endoscope insertion method between the cricoid cartilage 37 and the posterior wall of the hypopharynx 41 (FIG. 13A-C): the patient is placed in the left lateral or the left semiprone position. The mouthpiece is placed in the mouth. The gastroscope 28 is inserted through the mouthpiece into the oropharynx, and the gastroscope is rotated clockwise for positioning the gastroscope on the lateral side of the tongue, and the gastroscope is rotated counterclockwise for medially retracting the tongue with the gastroscope itself, and the gastroscope is inserted through the side of the tongue into the left pyriform sinus 35 while rotating the gastroscope counterclockwise, and the gastroscope is inserted into the esophagus 40 while rotating the gastroscope counterclockwise or clockwise. As shown in the figure, the white shaded portion of the gastroscope is inserted into the esophagus (see also, FIG. 15A, FIG. 15B, and FIG. 16). And the gastroscope is rotated clockwise or counterclockwise so as to observe the anterior wall of the esophagus in the 9 o'clock position, and the gastroscope is pulled while applying an upward angle for anteriorly retracting the cricoid cartilage 37, and the gastroscope is inserted between the cricoid cartilage and the posterior wall of the hypopharynx, and the postcricoid region and the posterior wall of the hypopharynx are examined, and the gastroscope is removed into the left pyriform sinus while rotating the gastroscope counterclockwise, and the left pyriform sinus is examined, and the gastroscope is inserted into the right pyriform sinus while rotating the gastroscope clockwise and applying an upward angle, and the right pyriform sinus is examined, and the gastroscope is pushed while applying a downward angle for anteriorly retracting the cricoid cartilage, and the gastroscope is inserted between the cricoid cartilage and the posterior wall of the hypopharynx, and the postcricoid region and the posterior wall of the hypopharynx are examined. Applying an upward angle is performed/achieved by rotating the control knob (up/down) with the left hand, as known in common practice (in other words, the holding portion of the endoscope is not manipulated with the right hand to apply an upward angle). And the gastroscope is removed into the left pyriform sinus while rotating the gastroscope counterclockwise, and the gastroscope is pushed while applying an upward angle for anteriorly retracting the cricoid cartilage, and the gastroscope is inserted between the cricoid cartilage and the posterior wall of the hypopharynx, and the postcricoid region and the posterior wall of the hypopharynx is examined.

Example 20

Tracheal tube insertion method, wherein the tongue 12 is medially retracted with the tracheal tube itself and the tracheal tube 38 forms a loop in the oral cavity, the oropharynx and the hypopharynx (FIG. 14A): the flexible endoscope is attached inside the tracheal tube. The patient is placed in the left lateral or the left semiprone position. The mouthpiece is placed in the mouth.

The tracheal tube is inserted through the mouthpiece into the oropharynx, and the tracheal tube is rotated clockwise for positioning the tracheal tube on the lateral side of the tongue, and the tracheal tube is rotated counterclockwise for medially retracting the tongue with the tracheal tube itself, and the tracheal tube is inserted through the side of the tongue into the left pyriform sinus 35 while rotating the tracheal tube counterclockwise, and the tip of the tracheal tube is turned to the glottis 39 by rotating the tracheal tube clockwise by 90 degrees so as to observe the glottis in the 9 o'clock position, and the tracheal tube is inserted into the trachea 42 while rotating the tracheal tube counterclockwise, and the flexible endoscope is detached from the tracheal tube, and the tracheal tube insertion is confirmed by cough reflex or respiratory sound.

Example 21

Tracheal tube insertion method, wherein the tongue is medially retracted with the tracheal tube itself and the tracheal tube 38 forms a loop in the oral cavity; the oropharynx and the hypopharynx, and the flexible endoscope is not attached to the tracheal tube: the patient is placed in the left lateral or the left semiprone position. The mouthpiece is placed in the mouth. The tracheal tube is inserted through the mouthpiece into the oropharynx, and the tracheal tube is rotated clockwise for positioning the tracheal tube on the lateral side of the tongue, and the tracheal tube is rotated counterclockwise for medially retracting the tongue with the tracheal tube itself, and the tracheal tube is inserted through the side of the tongue into the left pyriform sinus 35 while rotating the tracheal tube counterclockwise, and the tip of the tracheal tube is turned to the glottis 39 by rotating the tracheal tube clockwise by 90 degrees so as to observe the glottis in the 9 o'clock position, and the tracheal tube is inserted into the trachea while rotating the tracheal tube counterclockwise, and the tracheal tube insertion is confirmed by cough reflex or respiratory sound.

Example 22

Flexible gastroscope insertion method through the left pyriform sinus, wherein the tongue 12 is medially retracted with the flexible gastroscope itself and the flexible gastroscope 28 forms a loop in the oral cavity, the oropharynx and the hypopharynx (FIG. 15A): the patient is placed in the left lateral or the left semiprone position. The mouthpiece is placed in the mouth. The flexible gastroscope is inserted through the mouthpiece into the oropharynx, and the flexible gastroscope is rotated clockwise for positioning the flexible gastroscope on the lateral side of the tongue, and the flexible gastroscope is rotated counterclockwise for medially retracting the tongue with the flexible gastroscope itself, and the flexible gastroscope is inserted through the side of the tongue into the left pyriform sinus 35 while rotating the flexible gastroscope counterclockwise, and the flexible gastroscope is inserted into the esophagus 40 while rotating the flexible gastroscope counterclockwise or clockwise. (As shown in FIGS. 15 and 16, the gastroscope is inserted through the orifice of the esophagus).

Example 23

Flexible gastroscope insertion method through the right pyriform sinus, wherein the tongue 12 is medially retracted with the flexible gastroscope itself and the flexible gastroscope 28 forms a loop in the oral cavity, the oropharynx and the hypopharynx (FIG. 16): the patient is placed in the left lateral or the left semiprone position. The mouthpiece is placed in the mouth. The flexible gastroscope is inserted through the mouthpiece into the oropharynx, and the flexible gastroscope is rotated clockwise for positioning the flexible gastroscope on the lateral side of the tongue, and the flexible gastroscope is rotated counterclockwise for medially retracting the tongue with the flexible gastroscope itself, and the flexible gastroscope is inserted through the side of the tongue into the left pyriform sinus 35 while rotating the flexible gastroscope counterclockwise, and the tip of the flexible gastroscope is turned to the right pyriform sinus 36 by rotating the flexible gastroscope clockwise by 90 degrees so as to observe the glottis 39 in the 9 o'clock position, and the flexible gastroscope is inserted into the right pyriform sinus while rotating the flexible gastroscope clockwise by 90 degrees, and the flexible gastroscope is inserted into the esophagus 40 while rotating the flexible gastroscope clockwise.

DESCRIPTION OF THE REFERENCE
NUMERALS

1. Nasal cavity
2. Superior nasopharyngeal wall
3. Right torus tubarius
4. Pharyngeal orifice of the right Eustachian tube
5. Roof of the right nasal cavity
6. Right nasal cavity
7. Nasal septum
8. Roof of the left nasal cavity
9. Left nasal cavity
10. Right tonsillar fossa
11. Palatine uvula
12. Tongue
13. Right posterior palatine arch
14. Right anterior palatine arch
15. Right frontal sinus
16. Right anterior ethmoidal sinus ostium
17. Right maxillary sinus ostium
18. Right posterior ethmoidal sinus ostium
19. Right nasolacrimal duct ostium
20. Right sphenoidal sinus
21. Nasal plug
22. Right tympanic membrane 23. Left nasolacrimal duct ostium
24. Gall bladder
25. Liver
26. Common bile duct
27. Duodenum
28. Flexible endoscope
29. Median palatine suture
30. Maxillary linguogingival region
31. Lateral palatine region
32. Incisive papilla region
33. Looping of the flexible endoscope
34. Right Rosenmuller's fossa
35. Left pyriform sinus
36. Right pyriform sinus
37. Cricoid cartilage
38. Tracheal tube
39. Glottis
40. Esophagus
41. Posterior wall of the hypopharynx
42. Trachea

The invention claimed is:

1. A device insertion method, comprising inserting a device having a holding portion and a tip into a lumen of a hollow organ, the method further comprising:

(a) rotating a hollow organ by 45 to 135 degrees by changing a body position of a patient to a semilateral, lateral, or semiprone position for observing a lateral wall of a lumen of the hollow organ, wherein the body position was a supine, semi-recumbent, sitting, lithotripsy, or prone position, wherein if the patient is placed in the body position other than the semilateral, lateral, or semiprone position and the body position must be changed to the semilateral, lateral, or semiprone position during a procedure, the device remains inserted, or the device is removed, the body position is changed, and the device is reinserted, and if it is known from a beginning of the procedure that the lateral wall of the lumen of the hollow organ will be observed, the patient is placed in the semilateral, lateral, or semiprone position at the beginning of the procedure;

(b) inserting the device into the lumen while rotating a holding portion of the device clockwise or counterclockwise from the perspective of a person operating the device;

turning a tip of the device to the lateral wall of the lumen by rotating the holding portion of the device counterclockwise after inserting the device while rotating the holding portion of the device clockwise, or clockwise after inserting the device while rotating the holding portion of the device counterclockwise; and examining the lateral wall of the lumen;

(c) inserting the device into the lumen while rotating the holding portion of the device counterclockwise by 360 degrees from the perspective of a person operating the device, wherein the device forms a loop for avoiding contact with organs, securing the visual field or securing the insertion route;

(d) retracting an organ inside the hollow organ with the device itself by rotating the holding portion of the device counterclockwise or clockwise from the perspective of the person operating the device for securing the visual field or securing the insertion route, wherein the device is rotated counterclockwise or clockwise while the device is not pulled to prevent the effect of retraction from weakening;

(e) retracting the organ inside the hollow organ with the device itself by pulling or pushing the device while applying an upward angle for securing the visual field or securing the insertion route, wherein the device is pulled or pushed while the device is not rotated for preventing the effect of retraction from weakening; and (f) retracting the organ inside the hollow organ with the device itself by pushing the device while applying a downward angle for securing the visual field or securing the insertion route, wherein the device is pushed while the device is not rotated for preventing the effect of retraction from weakening.

2. The device insertion method according to claim 1, wherein the device is configured to increase the stiffness, the friction coefficient, or the diameter of the device, wherein the device used in the method is selected from the group consisting of:
  flexible endoscope,
  tracheal tube,
  ileus tube, and
  gastric tube.

3. The device insertion method according to claim 1, further comprising retracting the patient's tongue with the device itself for securing the insertion route, reducing gag reflex, and reducing sedatives, and the device forms a loop in the patient's oral cavity, oropharynx and hypopharynx,
comprising the steps of:
  placing the patient in the left lateral or the left semi-prone position;
  placing a mouthpiece in the patient's mouth;
  inserting the device through the mouthpiece into the oropharynx;
  rotating the holding portion of the device clockwise for positioning the device on a lateral side of the tongue;
  rotating the device counterclockwise for medially retracting the tongue with the device itself; and
  inserting the device through the side of the tongue into the patient's left pyriform sinus while rotating the device counterclockwise.

4. The device insertion method according to claim 1, further comprising retracting the patient's tongue with the device itself for securing the insertion route, reducing gag reflex, and reducing sedatives, and the device forms a loop in the patient's oral cavity, oropharynx and hypopharynx by rotating the device counterclockwise, wherein the device is not rotated clockwise,
comprising the steps of:
  placing the patient in the left lateral or the left semi-prone position;
  placing a mouthpiece in the patient's mouth;
  inserting the device through the mouthpiece along a lateral side of the tongue into the oropharynx while rotating the device counterclockwise;
  inserting the device along a lateral wall of the pharynx into the patient's left pyriform sinus while rotating the device counterclockwise.

5. The device insertion method according to claim 1, wherein the device is a flexible endoscope,
  further comprising observing the patient's hypopharynx including the patient's right pyriform sinus, left pyriform sinus, postcricoid region and posterior wall of the hypopharynx.

6. The device insertion method according to claim 5, further comprising observing the right pyriform sinus, wherein the patient's tongue is retracted with the flexible endoscope itself, and the flexible endoscope forms a loop in the oral cavity, the oropharynx and the hypopharynx,
comprising the steps of:
  placing the patient in the left lateral or the left semi-prone position;
  placing a mouthpiece in the patient's mouth;
  inserting the flexible endoscope through the mouthpiece into the oropharynx;
  rotating the flexible endoscope clockwise for positioning the flexible endoscope on a lateral side of the tongue;
  rotating the flexible endoscope counterclockwise for medially retracting the tongue with the flexible endoscope itself;
  inserting the flexible endoscope through the side of the tongue into the left pyriform sinus while rotating the flexible endoscope counterclockwise;
  turning the tip of the flexible endoscope to the right pyriform sinus by rotating the flexible endoscope clockwise by 90 degrees so as to observe the patient's glottis in a 9 o'clock position on a monitor displaying an endoscopic image, wherein a 12 o'clock position corresponds to an upward direction on the monitor;
  inserting the flexible endoscope into the right pyriform sinus; and
  examining the right pyriform sinus.

7. The device insertion method according to claim 5, further comprising observing the postcricoid region and the posterior wall of the hypopharynx, wherein the patient's tongue and the cricoid cartilage are retracted with the flexible endoscope itself, and the flexible endoscope forms a loop in the oral cavity, the oropharynx and the hypopharynx,
comprising the steps of:
  placing the patient in the left lateral or the left semi-prone position;
  placing a mouthpiece in the patient's mouth;
  inserting the flexible endoscope through the mouthpiece into the oropharynx;
  rotating the flexible endoscope clockwise for positioning the flexible endoscope on a lateral side of the tongue;
  rotating the flexible endoscope counterclockwise for medially retracting the tongue with the flexible endoscope itself;
  inserting the flexible endoscope through the side of the tongue into the left pyriform sinus while rotating the flexible endoscope counterclockwise;
  inserting the flexible endoscope into the esophagus while rotating the flexible endoscope counterclockwise or clockwise;
  rotating the flexible endoscope clockwise or counterclockwise so as to observe the anterior wall of the esophagus in a 9 o'clock position on a monitor displaying an endoscopic image, wherein a 12 o'clock position corresponds to an upward direction on the monitor;
  pulling the flexible endoscope while applying an upward angle for anteriorly retracting the cricoid cartilage;
  inserting the flexible endoscope between the cricoid cartilage and the posterior wall of the hypopharynx;
  examining the postcricoid region and the posterior wall of the hypopharynx;

removing the flexible endoscope into the left pyriform sinus while rotating the flexible endoscope counterclockwise;

examining the left pyriform sinus;

inserting the flexible endoscope into the right pyriform sinus while rotating the flexible endoscope clockwise and applying an upward angle;

examining the right pyriform sinus;

pushing the flexible endoscope while applying a downward angle for anteriorly retracting the cricoid cartilage;

inserting the flexible endoscope between the cricoid cartilage and the posterior wall of the hypopharynx;

examining the postcricoid region and the posterior wall of the hypopharynx;

removing the flexible endoscope into the left pyriform sinus while rotating the flexible endoscope counterclockwise;

pushing the flexible endoscope while applying an upward angle for anteriorly retracting the cricoid cartilage;

inserting the flexible endoscope between the cricoid cartilage and the posterior wall of the hypopharynx; and examining the postcricoid region and the posterior wall of the hypopharynx.

8. The device insertion method according to claim 1, wherein the device is a tracheal tube, further comprising inserting the tracheal tube in the left lateral or the left semiprone position, wherein the patient's tongue is retracted with the tracheal tube itself, and the tracheal tube forms a loop in the patient's oral cavity, oropharynx and hypopharynx, comprising the steps of:

attaching a flexible endoscope inside the tracheal tube;

placing the patient in the left lateral or the left semiprone position;

placing a mouthpiece in the patient's mouth;

inserting the tracheal tube through the mouthpiece into the oropharynx;

rotating the tracheal tube clockwise for positioning the tracheal tube on a lateral side of the tongue;

rotating the tracheal tube counterclockwise for medially retracting the tongue with the tracheal tube itself;

inserting the tracheal tube through the side of the tongue into the patient's left pyriform sinus while rotating the tracheal tube counterclockwise;

turning the tip of the tracheal tube to the patient's glottis by rotating the tracheal tube clockwise by 90 degrees so as to observe the glottis in a 9 o'clock position on a monitor displaying an endoscopic image, wherein a 12 o'clock position corresponds to an upward direction on the monitor:

inserting the tracheal tube into the patient's trachea while rotating the tracheal tube counterclockwise;

detaching the flexible endoscope from the tracheal tube; and confirming the tracheal tube insertion by cough reflex or respiratory sound.

9. The device insertion method according to claim 8, further comprising inserting the tracheal tube without attaching the flexible endoscope, wherein the tracheal tube can be inserted when a visual field cannot be secured due to bleeding, tumor, injury, or foreign body.

10. The device insertion method according to claim 1, wherein the device is a flexible gastroscope, further comprising inserting the flexible gastroscope through the patient's left pyriform sinus, wherein the patient's tongue is retracted with the flexible gastroscope itself, and the flexible gastroscope forms a loop in the patient's oral cavity, oropharynx and hypopharynx, comprising the steps of:

placing the patient in the left lateral or the left semiprone position;

placing a mouthpiece in the patient's mouth;

inserting the flexible gastroscope through the mouthpiece into the oropharynx;

rotating the flexible gastroscope clockwise for positioning the flexible gastroscope on a lateral side of the tongue;

rotating the flexible gastroscope counterclockwise for medially retracting the tongue with the flexible gastroscope itself;

inserting the flexible gastroscope through the side of the tongue into the left pyriform sinus while rotating the flexible gastroscope counterclockwise; and inserting the flexible gastroscope into the esophagus while rotating the flexible gastroscope counterclockwise or clockwise.

11. The device insertion method according to claim 1, wherein the device is a flexible gastroscope, further comprising inserting the flexible gastroscope through the patient's right pyriform sinus, wherein the patient's tongue is retracted with the flexible gastroscope itself, and the flexible gastroscope forms a loop in the patient's oral cavity, oropharynx and hypopharynx, comprising the steps of:

placing the patient in the left lateral or the left semiprone position;

placing a mouthpiece in the patient's mouth;

inserting the flexible gastroscope through the mouthpiece into the oropharynx;

rotating the flexible gastroscope clockwise for positioning the flexible gastroscope on a lateral side of the tongue;

rotating the flexible gastroscope counterclockwise for medially retracting the tongue with the flexible gastroscope itself;

inserting the flexible gastroscope through the side of the tongue into the patient's left pyriform sinus while rotating the flexible gastroscope counterclockwise;

turning the tip of the flexible gastroscope to the right pyriform sinus by rotating the flexible gastroscope clockwise by 90 degrees so as to observe the patient's glottis in a 9 o'clock position on a monitor displaying an endoscopic image, wherein a 12 o'clock position corresponds to an upward direction on the monitor;

inserting the flexible gastroscope into the right pyriform sinus while rotating the flexible gastroscope clockwise by 90 degrees; and inserting the flexible gastroscope into the esophagus while rotating the flexible gastroscope clockwise.

12. A flexible endoscope insertion method, comprising inserting a flexible endoscope having a holding portion and a tip into a body cavity, the method further comprising:

(a) rotating a body cavity by 0 to 90 degrees by changing a patient's body position to a desired position for observing a lateral side of an organ in the body cavity, wherein if the body position must be changed during a procedure, the flexible endoscope is remain inserted, or the flexible endoscope is removed, the body position is changed, and the flexible endoscope is reinserted, and if it is known from a beginning of the procedure that the lateral side of the organ in the body cavity will be observed, the patient is placed in the desired position at the beginning of the procedure;

(b) inserting the flexible endoscope toward the organ while rotating an insertion portion of the flexible endoscope clockwise or counterclockwise from the perspective of a person operating the flexible endoscope;

turning a tip of the flexible endoscope to the lateral side of the organ by rotating the holding portion of the flexible endoscope counterclockwise after inserting the flexible endoscope while rotating the holding portion of the flexible endoscope clockwise, or rotating the holding portion of the flexible endoscope clockwise after inserting the flexible endoscope while rotating the holding portion of the flexible endoscope counterclockwise; and examining the lateral side of the organ;

(c) inserting the flexible endoscope toward the organ inside the body cavity while rotating the insertion portion of the flexible endoscope counterclockwise by 360 degrees from the perspective of a person operating the flexible endoscope, wherein the flexible endoscope forms a loop for avoiding contact with organs, securing the visual field or securing the insertion route;

(d) retracting an organ inside the body cavity with the flexible endoscope itself by rotating the insertion portion of the flexible endoscope counterclockwise or clockwise from the perspective of the person operating the endoscope for securing the visual field or securing the insertion route, wherein the flexible endoscope is rotated counterclockwise or clockwise while the flexible endoscope is not pulled to prevent the effect of retraction from weakening;

(e) retracting an organ inside the body cavity with the flexible endoscope itself by pulling or pushing the flexible endoscope while applying an upward angle for securing the visual field or securing the insertion route, wherein the flexible endoscope is pulled or pushed while the flexible endoscope is not rotated to prevent the effect of retraction from weakening; and (f) retracting an organ inside the body cavity with the flexible endoscope itself by pushing the flexible endoscope while applying a downward angle for securing the visual field or securing the insertion route, wherein the flexible endoscope is pushed while the flexible endoscope is not rotated to prevent the effect of retraction from weakening.

13. The flexible endoscope insertion method according to claim 12, wherein the flexible endoscope is configured such that the organ can be readily retracted by increasing the stiffness, the friction coefficient, or the diameter of the insertion portion of the flexible endoscope.

14. The flexible endoscope insertion method according to claim 12, further comprising a natural orifice transluminal cholecystectomy, wherein the patient's duodenum, transverse colon, and greater omentum are retracted with the flexible endoscope itself, comprising the steps of:

inserting the flexible endoscope through the patient's anus into the patient's large intestine;

projecting a surgical device from the tip of the flexible endoscope;

incising a wall of the large intestine;

inserting the flexible endoscope through the wall of the large intestine into an abdominal cavity;

inserting the flexible endoscope around the patient's common bile duct;

turning the tip of the flexible endoscope to a right lateral side of the common bile duct by rotating the flexible endoscope counterclockwise, and simultaneously, medially and inferiorly retracting the duodenum, transverse colon, and greater omentum with the flexible endoscope itself to distend the common bile duct by rotating the flexible endoscope counterclockwise for securing the broader operative field;

exposing a cystic duct and cystic artery in a right lateral side of the distended common bile duct;

ligating and incising the cystic duct and cystic artery; and resecting the patient's gallbladder.

\* \* \* \* \*